(12) United States Patent
Leong et al.

(10) Patent No.: US 6,852,709 B2
(45) Date of Patent: Feb. 8, 2005

(54) BIOLOGICALLY USEFUL POLYPHOSPHATES

(75) Inventors: Kam Leong, Ellicott City, MD (US);
Wen Jie, Baltimore, MD (US);
Hai-Quan Mao, Coast Crescent (SG)

(73) Assignee: Johns Hopkins University, Baltimore, MD (US)

( * ) Notice: Subject to any disclaimer, the term of this patent is extended or adjusted under 35 U.S.C. 154(b) by 393 days.

(21) Appl. No.: 09/871,602

(22) Filed: May 31, 2001

(65) Prior Publication Data

US 2002/0045263 A1 Apr. 18, 2002

Related U.S. Application Data

(60) Provisional application No. 60/208,262, filed on May 31, 2000.

(51) Int. Cl.[7] .................. A01N 57/00; A01N 43/04; C12N 15/63; C12N 15/88; A61K 9/00
(52) U.S. Cl. .................. 514/75; 435/455; 435/458; 435/320.1; 424/400; 424/500; 514/44; 536/23.1
(58) Field of Search .................. 514/75, 44; 424/400, 424/500; 435/455, 458, 320.1; 536/23.1

(56) References Cited

U.S. PATENT DOCUMENTS 5,846,923 A * 12/1998 Reierson .................. 510/467
5,952,451 A    9/1999 Zhao

FOREIGN PATENT DOCUMENTS

EP    0 386 757 A2    3/1990
WO    WO 98/46286    10/1998

OTHER PUBLICATIONS

Korematsu et al. Polymer Bulletin, 1997; 38:133–40.*
Mahato et al. Crit. Rev. Ther. Drug Carr. Syst., 1997; 14(2):133–72.*
Nakaya et al. Macromol. 1989; 22:3180–1.*
Yamada et al. J.M.S.—Pure Appl. Chem., 1995; A32(10):1723–33.*
Li et al. Macromo. Rapid. Comm., 1996; 17:737–44.*

* cited by examiner

Primary Examiner—Gerry Leffers
Assistant Examiner—Ramin Akhavan
(74) Attorney, Agent, or Firm—Peter F. Corless; John B. Alexander; Edwards & Angell, LLP

(57) ABSTRACT

The present invention provides biodegradable polymers, polymer compositions, particles composed thereof and methods of using same for the controlled release of a biologically active substance to a specified tissue or cells. Preferred polymers include biodegradable, amphiphilic polyphosphates which are capable of complexing one or more biologically active substances. Preferred methods include the controlled release of biologically active substances and gene therapy using polymers and nanoparticles composed thereof.

34 Claims, 9 Drawing Sheets

Figure 1. Proton NMR spectrum for (2).
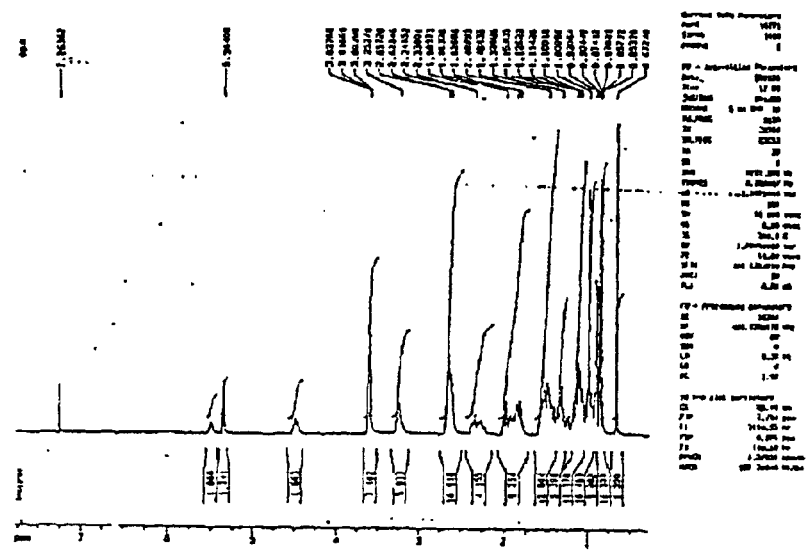
Figure 2. Proton NMR spectrum for (3).
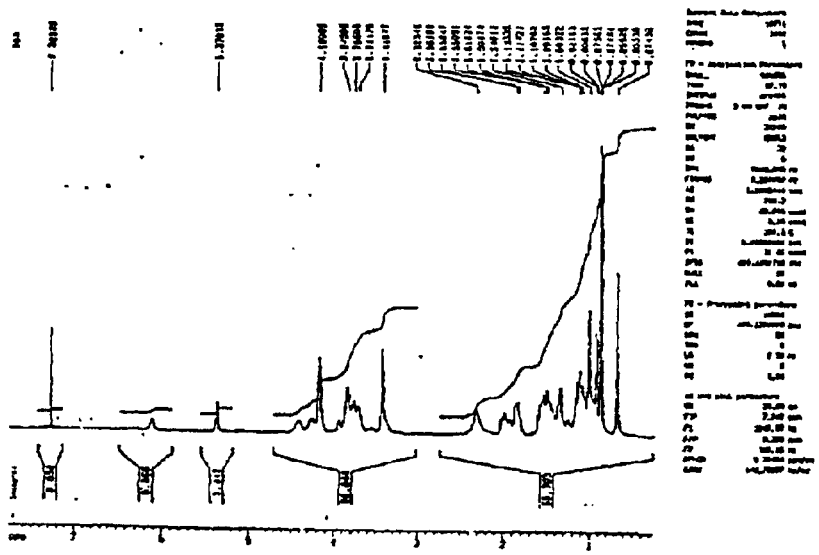

Figure 3. NMR spectrum for PCEP.
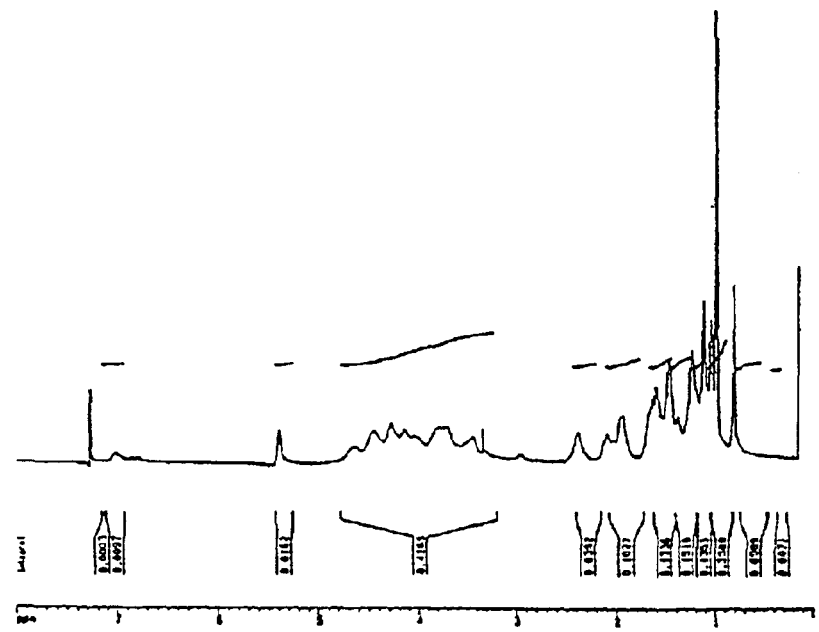
Figure 4. GPC graph for PCEP.
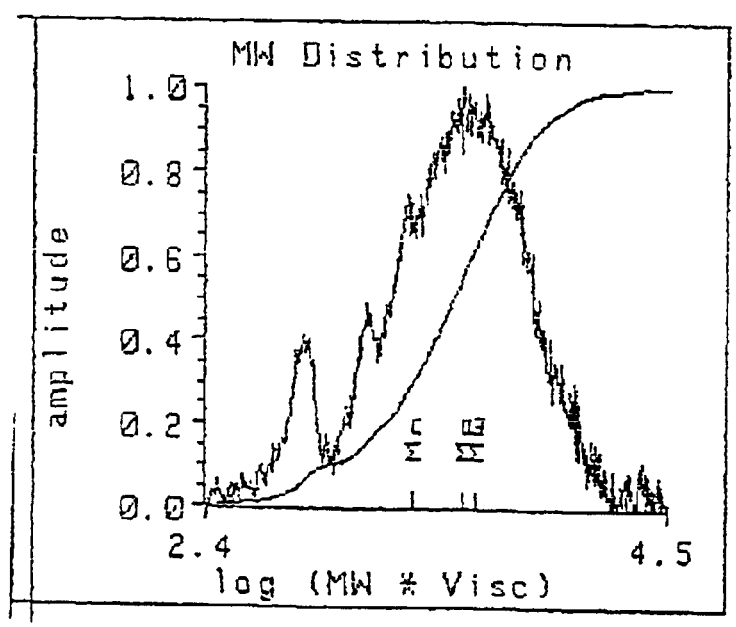

Figure 5. Cytotoxicity of PCEP on HeLa cells.
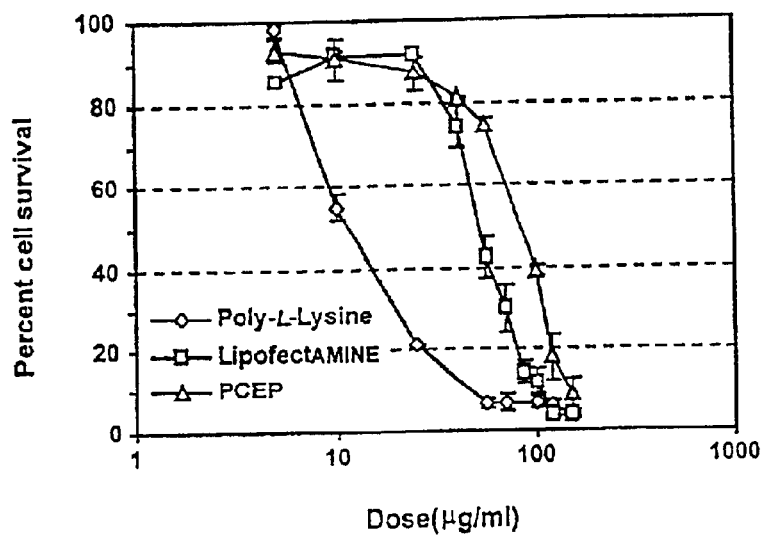
Figure 6. Size report of PCEP micelles.
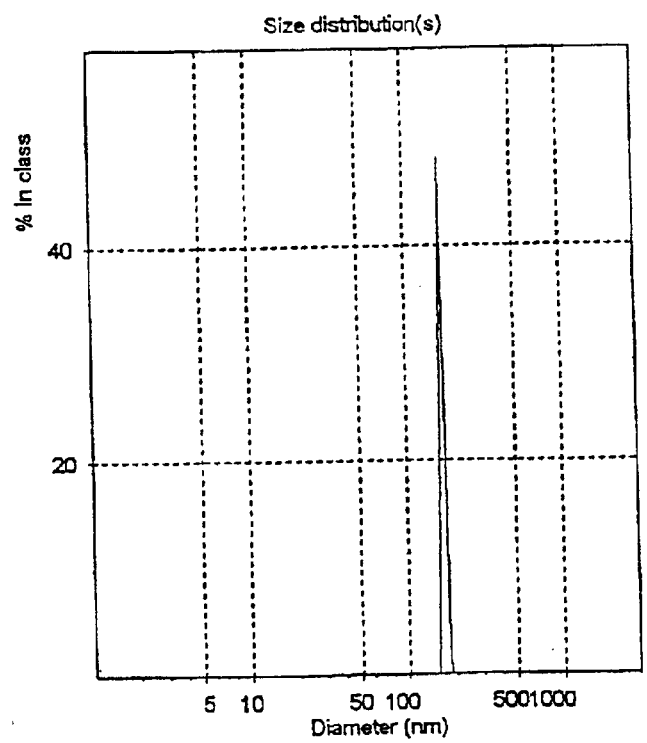

Figure 7. Effect of PCEP/DNA ratio on the average size of complexes.
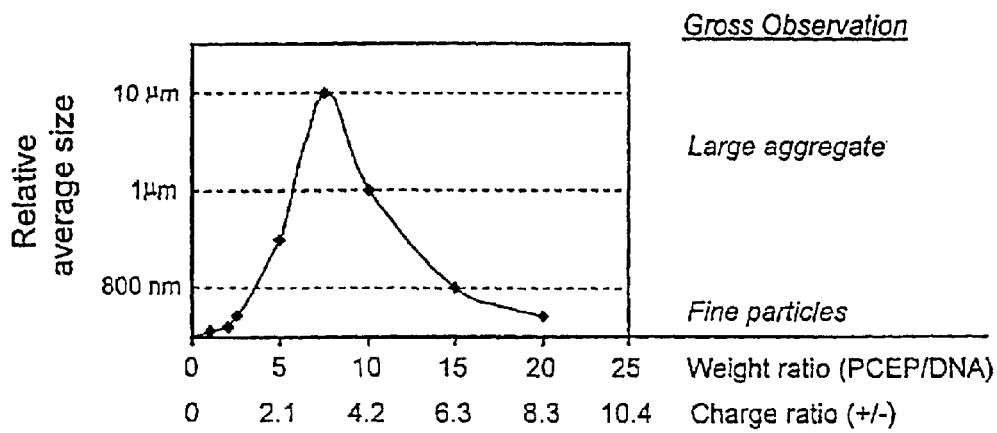
Figure 8. Size report of PCEP-DNA complexes.
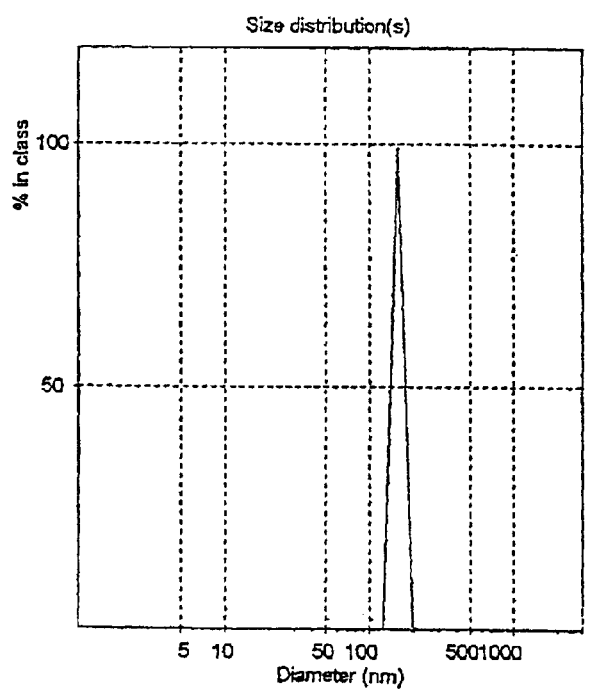

Figure 9. Agrose electrophoresis of pRE-Luciferase DNA after complexed with PPEC.
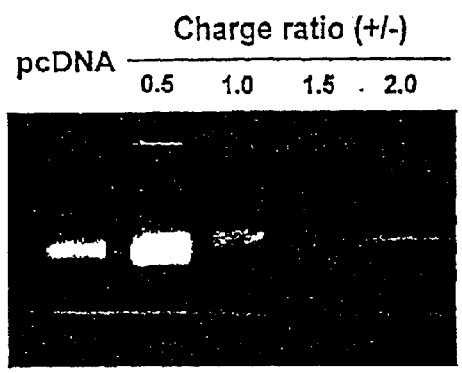
Figure 10. Preparation condition on the transfection efficiency
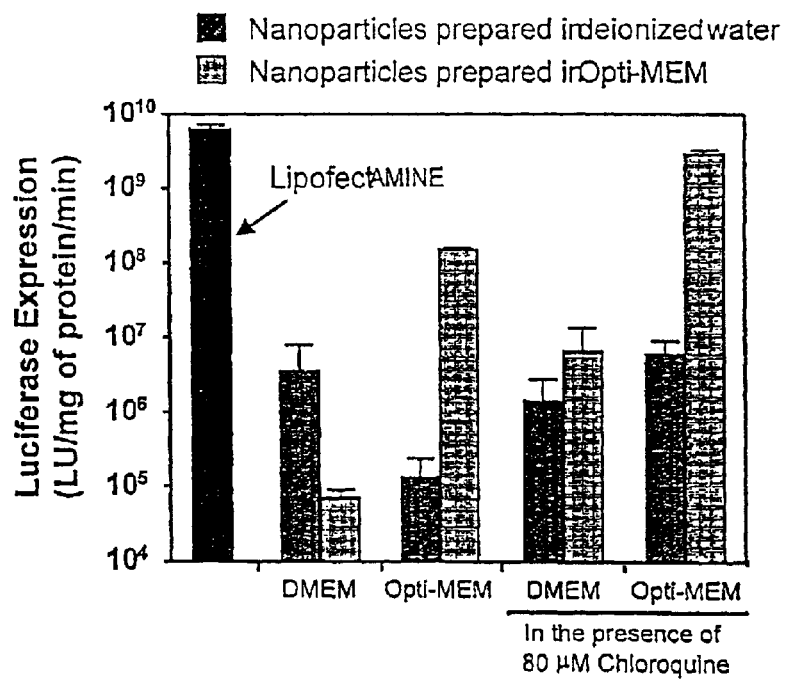

Figure 11. Effect of chloroquine on transfection efficiency of the PCEP-DNA nanoparticles

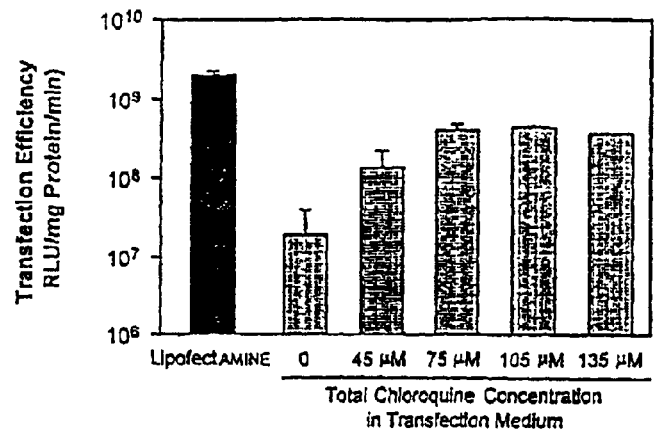

Figure 12. Preparation condition on the transfection efficiency

⬛ Protocol 1: CQ was incubated with PCEP before complexed with pcDNA

▦ Protocol 2: CQ was incubated with pcDNA before complexed with PCEP

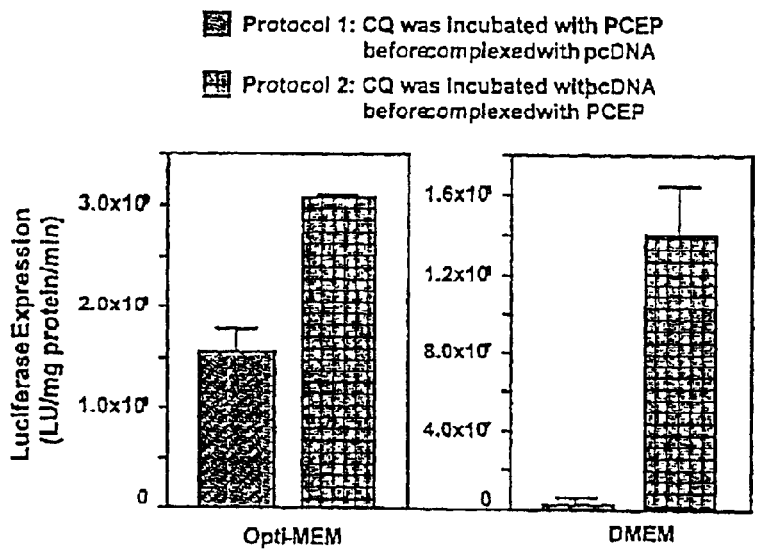

Figure 13. Effect of charge ratio on transfection efficiency of the PCEP-DNA nanoparticles

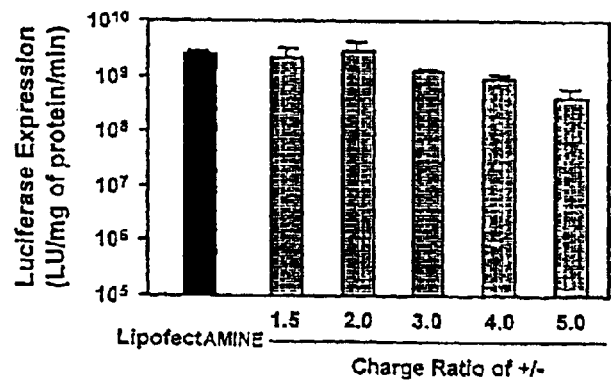

Figure 14. Dose response of transfection efficiency of the PCEP-DNA complexes.
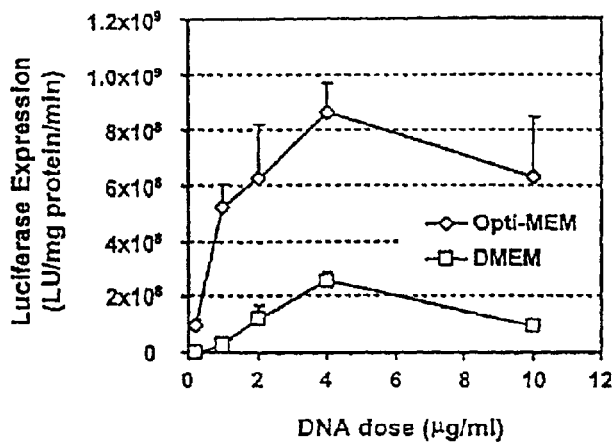
Figure 15. Effect of charge ratio on transfection efficiency of the PCEP-DNA complexes or HeLa cells.
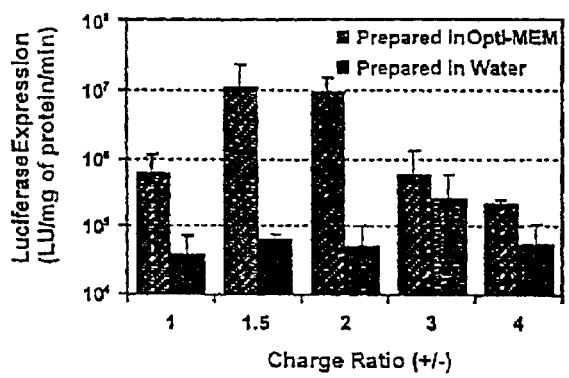
Figure 16. Transfection efficiency of the PCEP-DNA complexes on CaCO-2 cells.
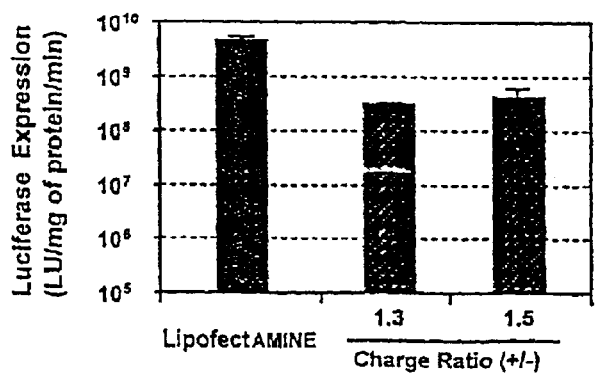

Figure 17. Storage stability of PCEP-DNA complexes. The complexes were stored at different temperature for three days before the transfection was performed.
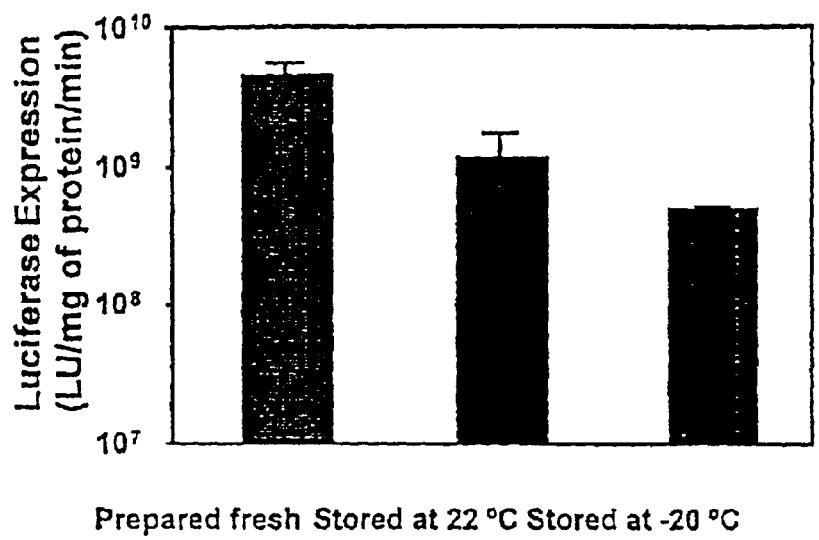

BIOLOGICALLY USEFUL POLYPHOSPHATES

This application claims the benefit of U.S. Provisional Application Serial No. 60/208,262 filed May 31, 2000, the teachings of which are incorporated herein by reference.

This invention was supported by funding of the National Institute of Health. The United States Government has certain rights to the invention.

BACKGROUND OF THE INVENTION

1. Field of the Invention

The present invention generally relates to a method of delivering bioactive substances, particularly nucleic acids, into cells. This invention describes a series of novel biodegradable polyphosphoesters as transport agents. Preferred polymers of the invention self assemble in aqueous buffer at room temperature into micelles. Negative charged molecules, e.g. plasmid DNA form complex with these vesicles. Drugs or molecules that can be delivered using these polymeric systems range from DNA plasmids, RNAs, proteins to small molecular weight drugs. Polymers of the invention can also be used to aid the virus particle mediated gene transfer.

2. Background

Effective delivery of nucleic acid to cells or tissue with high levels of expression are continued goals of gene transfer technology. As a consequence of the general inability to achieve those goals to date, however, clinical use of gene transfer methods has been limited.

Ideal gene delivery vehicles should be bioabsorable, non-toxic, non-immunogenic, stable during storage and after administration, able to access target cells, and suitable for efficient gene expression. As many studies demonstrate, the limitations of viral vectors make synthetic vectors an attractive alternative.

Cationic liposome (Lipoplex) and cationic polymers are among the two major types of non-viral gene delivery vectors. Toxicity data on cationic polymers suggests that many polymers used for transfections are most effective at concentrations that are just subtoxic. illustrative polymers include polyamino acids (e.g. poly-L-lysine, poly-L-ornithine), polyamidoamine dendrimers, chitosan, polyethylenimine, poly((2-dimethylamino)ethyl methacrylate). The entry of the complexes may be mediated by the membrane destabilizing effects of cationic polymers. Several observations have suggested that liposomal systems are relatively unstable after the administration. Significant toxicity has been shown to be associated to liposomal vectors, especially the fusogenic phospholipid (neutral lipid), include the down regulation of PKC dependent immunomodulator synthesis, macrophage toxicity, neurotoxicity, acute pulmonary inflammation, etc. Moreover, both vectors are far less efficient comparing with the viral counter-part. Searching for a safe and efficient gene carrier will still remain a major challenge in the field of non-viral gene delivery.

Biocompatible polymeric materials have been used extensively in therapeutic drug delivery and medical implant device applications. Sometimes, it is also desirable for such polymers to be, not only biocompatible, but also biodegradable to obviate the need for removing the polymer once its therapeutic value has been exhausted.

Conventional methods of drug delivery, such as frequent periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more nearly maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally and in a controlled fashion, see Langer et al., Rev. Macro. Chem. Phys., C23(1), 61 (1983). As a result, less total drug is required, and toxic side effects can be minimized. Polymers have been used as carriers of therapeutic agents to effect a localized and sustained release. See Chien et al., Novel Drug Delivery Systems (1982). Such delivery systems offer the potential of enhanced therapeutic efficacy and reduced overall toxicity.

SUMMARY OF THE INVENTION

The present invention provides a new class of polyphosphates, polyphosphate particles particularly nanoparticles such as micelles, compositions comprising a polyphosphate nanoparticle such as a micelle and at least one bioactive substance and methods of preparing and using such polymer micelles and compositions to deliver bioactive substances to specified tissues or cells. A preferred application includes the localized, controlled release of at least a portion of one or more bioactive substances from a polyphosphate nanoparticle of the invention into a specified tissue or cell. In another preferred application, polyphosphate compositions and nanoparticles of the invention are effective gene delivery agents for localized delivery of DNA to specified tissues or cells in gene therapy.

The invention provides biodegradable amphiphilic polyphosphates. Preferred polyphosphates have at least one phosphate group in the main chain of the polymer and the polymer includes at least one positively charged or positively chargeable group and at least one hydrophobic moiety. Further preferred polyphosphates of the invention are biocompatible before, during and upon biodegredation.

The invention also provides nanoparticles, particularly micelles, of the biodegradable, amphiphilic polyphosphate of the invention. Preferred micelles include those comprising a polyphosphate having at least one phosphate group in the main chain of the polymer and the polymer preferably having at least one positively charged or positively chargeable group and at least one hydrophobic moiety. Preferred nanoparticles are about 50 nm to about 500 nm in size. Particularly preferred nanoparticles are micelles have diameters from about 50 nm to about 500 nm or from about 75 nm to about 300 nm.

The invention further includes methods of making biodegradable amphiphilic polyphosphates of the invention. Preferred methods are suitable for the preparation of polyphosphates having at least one phosphate group in the main chain of the polymer and the polymer having at least one positively charged group or positively chargeable and at least one hydrophobic moiety, the method comprising:

providing at least one diol monomer and at least one phosphate precursor monomer; and reacting the diol monomer(s) and phosphate precursor monomer(s) under conditions conducive to the formation of a biodegradable amphiphilic polyphosphate.

The invention further includes methods of preparing a biodegradable amphiphilic polyphosphate nanoparticles. In a preferred method of making polyphosphate micelles, the invention comprises:

providing a biodegradable amphiphilic polyphosphate having at least one phosphate group in the main chain of the polymer and the polymer having at least one positively charged or positively chargeable group and at least one hydrophobic moiety; and agitating a colloidal suspension of the polymer in a biphasic solution to obtain micelles having a diameter of between about 50 nm and about 500 nm, more preferably from about 100 nm to about 400 nm or from about 150 nm to about 300 nm.

The invention also includes methods of preparing compositions comprising a biodegradable amphiphilic polyphosphate and a biologically active substance. Preferred methods typically result in the formation of nanoparticles of the composition and comprises the steps of:

providing at least one biodegradable amphiphilic polyphosphate micelle and at least one biologically active substance; and contacting the micelle with the biologically active substance under conditions conducive to the inclusion of at least a portion of the biologically active substances into the micelles resulting in a biodegradable micelle composition comprising a biologically active substance.

In yet another aspect, the invention provides methods for the controlled release of a biologically active substance preferably comprising steps of:

providing a biodegradable amphiphilic polyphosphate micelle composition comprising:

(a) at least one biologically active substance; and (b) a biodegradable amphiphilic polyphosphate micelle having at least one phosphate group in the main chain of the polymer and the polymer preferably having at least one positively charged or positively chargeable group and at least one hydrophobic moiety;

contacting the micelle composition in vivo or in vitro with a biological fluid, cell or tissue under conditions conducive to the delivery of at least a portion of the biologically active substance to the biological fluid, cell or tissue so that the biologically active substance is released in a controlled manner.

The invention also provides methods for gene therapy, wherein a gene or gene fragment, e.g., a DNA sequence is transfected in a controlled fashion into a specified tissue or cells. The method comprising the steps of:

providing a biodegradable amphiphilic polyphosphate micelle composition comprising:

(a) at least a portion of at least one gene; and (b) a biodegradable amphiphilic polyphosphate micelle having at least one phosphate group in the main chain of the polymer and the polymer having at least one positively charged group and at least one hydrophobic moiety;

contacting the micelle composition in vivo or in vitro with a biological fluid, cell or tissue under conditions conducive to the delivery of at least a portion of the gene to the biological fluid, cell or tissue, and preferably where expression of the gene can occur.

BRIEF DESCRIPTION OF THE DRAWINGS

FIG. 1 is a $^1$H NMR spectrum of Cholesteryl (2-[bis(2-hydroxyethyl)-amino]ethyl) carbamate;

FIG. 2 is a $^1$H NMR spectrum of Cholesterol (2-[bis(2-hydroxyethyl)-ammnium]ethyl) carbamate iodide;

FIG. 3 is a $^1$H NMR spectrum of PCEP;

FIG. 4 is a gel permeation chromatogram (GPC) of PCEP;

FIG. 5 is a plot of cytotoxicity of PCEP on HeLa cells;

FIG. 6 is a plot of PCEP micelle size distribution;

FIG. 7 is a plot of the ratio of PCEP-DNA on the average size of micelles formed of PCEP-DNA complexes;

FIG. 8 is a plot of the size distribution of micelles composed of PCEP-DNA complexes;

FIG. 9 is an Agrose electrophoresis of pRE-Luciferase DNA after complexation with PPEC;

FIG. 10 is a bar graph of transfection efficiency of nanoparticles prepared under different conditions;

FIG. 11 is a bar graph of transfection efficiency of PCEP-DNA nanoparticles at various concentrations of chloroquine;

FIG. 12 is a bar graph of transfection efficiency of PCEP-DNA-chloroquine nanoparticles prepared under different conditions;

FIG. 13 is a bar graph of the effect of charge ratio on transfection efficiency of the PCEP-DNA nanoparticles;

FIG. 14 is a plot of transfection efficiency of PCEP-DNA complexes as a function of DNA dose;

FIG. 15 is a bar graph of the effect of charge ratio on transfection efficiency of the PCEP-DNA complex nanoparticles on HeLa cells;

FIG. 16 is a bar graph of transfection efficiency of the PCEP-DNA complex nanoparticles on CaCO-2 cells;

FIG. 17 is a bar graph of storage stability of PCEP-DNA complexes at different temperatures over three days prior to using the complexes as transfection agents.

DETAILED DESCRIPTION OF THE INVENTION

Figure 18:
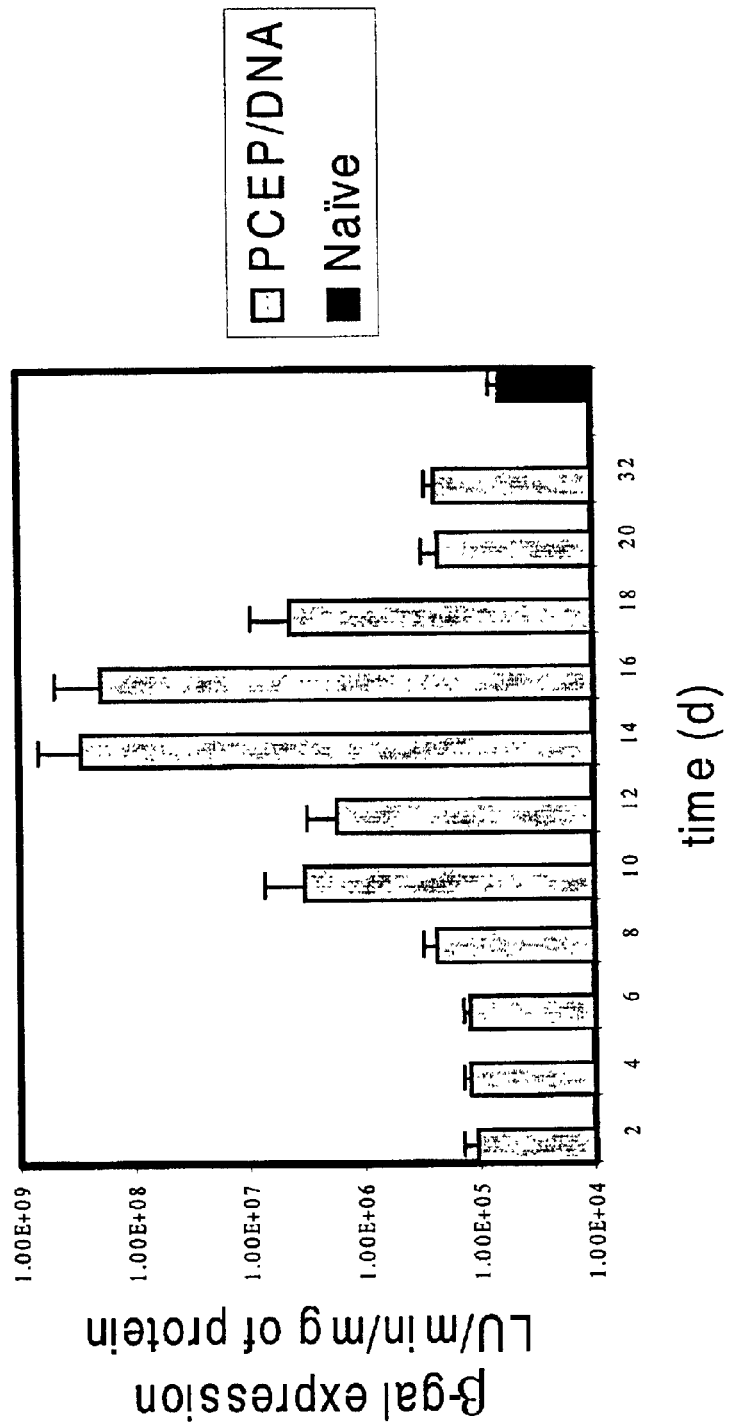
FIG. 18 is a bar graph of gene expression of β-gal in tibialis muscle of BALB/C mice transfected with pLacZ plasmid (5 µg DNA/leg).

The present invention features biodegradable polymers, polymer compositions comprising a biodegradable polymer and a biologically active substance and articles prepared therefrom which are suitable for use in the localized, controlled release of a biologically active substance at a specified tissue or cells and for use in gene therapy.

The invention provides biodegradable, amphiphilic polyphosphates having at least one phosphate group in the main chain of the polymer and the polymer preferably having at least one positively charged group and at least one hydrophobic moiety. Typically polyphosphates of the invention have between about 1 or 5 and about 2,000 phosphate groups in the backbone and have a molecular weight of between about 500 or 1000 and 1,000,000. Suitable polyphosphates of the invention include those that have between about 10 and about 100, 200, 300, 400, 500, 600, 700, 800, 900, or 1000 phosphate groups in the polymer main chain and a molecular weight of between about 1,000 and about 50,000, 100,000, 200,000, 300,000, 400,000, 500,000, 600,000, 700,000, 800,000 or 900,000. Further, as discussed above, preferred polyphosphates of the invention have a net positive charge. Further, polyphosphates of the invention self-aggregate into meso-stable phases such as lamellar or micellar phases. Particularly preferred are biodegradable amphiphilic polyphosphates that self-assemble into nanoparticles such as micelles with an average particle size of between about 50 nm and 500 nm. Furthermore polyphosphates of the invention are typically biocompatible and/or non-toxic before, during and after biodegradation processes occur.

Preferred amphiphilic polyphosphates of the invention comprise positively charged or positively chargeable groups which are integral to the main chain of the polymer or are present in a phosphate side chain group. Typical charged or positively chargeable groups include acid conjugates of primary, secondary and tertiary amines, quaternary ammonium groups and quaternary phosphonium groups. Other positively charged or positively chargeable groups which are positively charged in physiological media and are biocompatible are also contemplated within the scope of the present invention.

Preferred amphiphilic polyphosphates of the invention comprise hydrophobic moieties which are pendant from the polymer main chain. Typically each hydrophobic group is pendant from a phosphate group or a charged group that is integral to the main-chain of the polymer. Preferred hydrophobic groups are biocompatible and include aliphatic hydrocarbons such as higher alkyl groups which can include one to about 5 rings and steroid derivatives, particularly sterols such as cholesterol, cholesterol derivatives and cholesterol analogs.

Other polyphosphates provided by the invention further comprise a hydrophilic group which can be neutral or charged, the hydrophilic group either can be integral to the polymer main chain or can be a pendant group that is linked to the main chain. Preferred hydrophilic groups include groups with one or more functional groups selected from ether, ester, amide, urea, urethanes, amine, carboxylate, and other polar groups. Particularly preferred hydrophilic groups include poly(ethylene glycol) alkyl ethers such as PEG ethers of the formula —(CH$_2$CH$_2$O)$_x$CH$_2$CH$_2$— and —(CH$_2$CH$_2$O)$_x$CH$_2$CH$_3$.

Additionally preferred polyphosphates provided by the invention additionally include one or more side chains that comprise at least one targeting groups that are capable of facilitating cellular uptake. Preferred targeting groups include cell permeating material, mannose, transferin, peptides which facilitate endosomal disruption and the like.

Preferred biodegradable amphiphilic polyphosphates of the invention comprise repeat units as in Formula I:

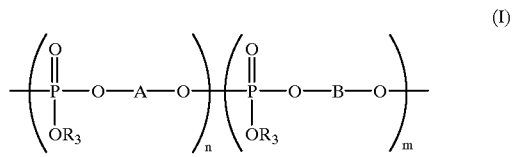

(I)

wherein

A and B can be the same or different and are each independently selected from the group consisting of optionally substituted alkylene, optionally substituted cyclic alkylene, optionally substituted arylene, optionally substituted heteroarylene, optionally substituted cyclic heteroalkylene, a hydrophilic divalent linker group, and (CH$_2$CH$_2$O)$_x$CH$_2$CH$_2$, such that A, B or both A and B comprise a positively chargeable functional group in the mainchain and A, B or both A and B can be optionally substituted with one or more neutral or charged hydrophilic groups or hydrophobic groups;

x is an integer from about 1 to about 100;

R$_3$ is optionally substituted alkyl, optionally substituted aryl, optionally substituted heteroaryl, optionally substituted heteroalicyclic, optionally substituted cycloalkyl, optionally substituted aralkyl or optionally substituted cycloalkylalkyl; and each occurrence of R$_3$ can be optionally substituted with one or more neutral or charged groups or one or more hydrophobic moieties;

m and n are independently selected non-negative integers; and m+n≧1.

Preferred polymers of formula I have the sum of m+n between about 5 and 2,000, more preferably between about 10 and 1,000 or between about 10 and 500. Also preferred are polymers of formula I wherein x is between about 5 and 50 or between 5 and 20.

Additionally preferred polymers according to formula I include polymers according to formula II:

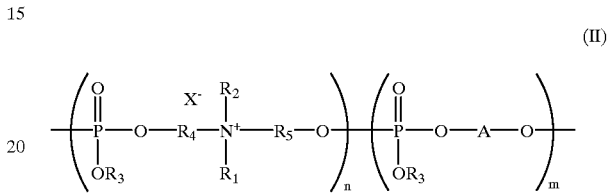

(II)

wherein

R$_4$, R$_5$ and A are each independently chosen from the group consisting of optionally substituted alkylene, optionally substituted cycloalkylene, divalent neutral or charged hydrophilic moieties, —(CH$_2$CH$_2$O)$_x$CH$_2$CH$_2$;

x is an integer from 1 to about 100;

R$_1$ is hydrogen, optionally substituted alkyl, optionally substituted alkenyl, optionally substituted alkynyl, optionally substituted cycloalkyl, optionally substituted cycloalkylalkyl, optionally substituted aralkyl, optionally substituted heteroalicyclic, or (CH$_2$)$_a$—Y—Z group wherein Y is an —O—, —CO$_2$—, —NHCO$_2$—, or —OCO$_2$— functional group and Z is optionally substituted alkyl, optionally substituted alkenyl, optionally substituted alkynyl, optionally substituted cycloalkyl, optionally substituted cycloalkylalkyl, optionally substituted aralkyl, poly(ethylene glycol)-alkyl ether or a steroid derivative;

R$_2$ is independently selected at each occurrence to be absent, hydrogen, optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl; and X$^-$ is absent or is a counter ion, preferably a biocompatible anion, i.e., X$^-$ is present where the polymer comprises a charged group.

Additionally preferred polymers according to formula I include polymers according to formula III:

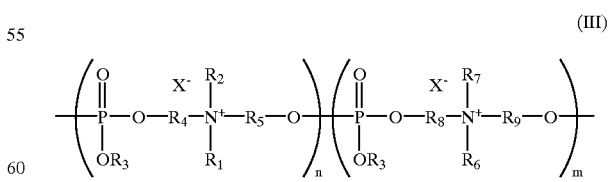

(III)

wherein

R$_4$, R$_5$, R$_8$ and R$_9$ are independently selected at each occurrence from the group consisting of optionally substituted alkylene, optionally substituted cycloalkylene, and poly(ethyleneglycol) alkyl ether, each occurrence of R$_4$, R$_5$, $R_8$ and $R_9$ can be optionally substituted with a neutral or charged hydrophilic group selected from the group consisting of hydroxyl, hydroxyalkyl, aminoalkyl, N-alkyl aminoalkyl, N,N-dialkyl aminoalkyl, amino, N-alkylamino, N,N-dialkylamino, N,N,N-trialkylamino, amide, carboxylate, sulfate, phosphate and the like;

$R_2$ and $R_7$ are each independently selected groups chosen at each occurrence to be absent, hydrogen, optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl;

$R_3$ is independently selected at each occurrence to be optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl;

$R_1$ and $R_6$ are each independently selected groups chosen at each occurrence from the group consisting of hydrogen, optionally substituted alkyl, poly(ethylene glycol) alkyl ether, $(CR_{10}R_{11})_b$—Y—Z wherein Y is —$OCO_2$— or —$NR_{10}CO_2$—, Z is alkyl, poly(ethylene glycol) alkyl ether or a steroid derivative;

$R_{10}$ and $R_{11}$ are each independently selected at each occurrence from the group consisting of hydrogen and optionally substituted alkyl;

b is a positive integer, preferably b is an integer in the range of about 1 to about 20, about 1 to about 16, about 1 to about 12, about 1 to about 8 or about 1 to about 6;

$X^-$ is absent or is a counter ion, preferably a biocompatible anion, i.e., $X^-$ is present where the polymer comprises a charged group;

$m+n \geq 1$; and $n \geq 1$.

Additionally preferred polymers according to formula I include polymers according to formula IV:

$$\left(\begin{array}{c} O \\ \| \\ -P-O-(CH_2)_a-\overset{R_2}{\underset{R_1}{N^+}}-(CH_2)_a-O- \\ | \\ OR_3 \end{array}\right)_n \left(\begin{array}{c} O \\ \| \\ -P-O-(CH_2)_a-\overset{R_7}{\underset{R_6}{N^+}}-(CH_2)_a-O- \\ | \\ OR_3 \end{array}\right)_m \quad (IV)$$

wherein $R_2$ and $R_7$ are each independently selected to be absent, hydrogen or optionally substituted alkyl;

$R_1$ and $R_6$ are each independently selected at each occurrence to be hydrogen, optionally substituted higher alkyl or $(CH_2)_b$—$N(R_{10})CO_2$—Z;

$R_{10}$ is independently chosen at each occurrence to be hydrogen or optionally substituted lower alkyl groups;

Z is independently chosen at each occurrence of Z to be optionally substituted alkyl, $(CH_2CH_2O)_xCH_2CH_3$ or a steroid derivative;

a is an positive integer, preferably a is independently selected at each occurrence of a in the formula to be an integer from about 1 to about 20, from 1 to about 16, from 1 to about 12, from 1 to about 8, or from 1 to about 6;

b is a positive integer, preferably b is an integer in the range of about 1 to about 20, about 1 to about 16, about 1 to about 12, about 1 to about 8 or about 1 to about 6;

x is an integer from about 1 to about 100; and each $X^-$ is absent or is a counter ion, preferably a biocompatible anion, i.e., $X^-$ is present where the polymer comprises a charged group.

Particularly preferred polyphosphate according to formula III or IV comprise a hydrophobic $R_1$ group such as a cholesterol derivative or a straight chain higher alkyl group and a $R_6$ group such as a hydrophilic poly(ethylene glycol) derivative or a hydrophobic lower alkyl group. Particularly suitable $R_1$ and $R_6$ groups include:

$R_1 = $ —$(CH_2)_2$—NH—C(=O)—O—[cholesterol];

—$(CH_2)_{15}CH_3$ $R_6 = $ —$(CH_2)_2$—NH—C(=O)—O—$(CH_2CH_2O)_x$—$CH_2CH_2$—$CH_3$; —$CH_3$

Additionally preferred polymers according to formula I include polymers according to formula V:

$$\left(\begin{array}{c} O \\ \| \\ -P-O-R_4-\overset{R_2}{\underset{R_1}{N^+}}-R_5-O- \\ | \\ OR_3 \end{array}\right)_n \quad (V)$$

wherein $R_1$ is independently selected groups chosen at each occurrence from the group consisting of hydrogen, optionally substituted higher alkyl, poly(ethylene glycol) alkyl ether, and —$(CR_{10}R_{11})_b$—Y—Z Y is —$OCO_2$— or —$NR_{10}CO_2$—;

Z is optionally substituted alkyl, poly(ethylene glycol) alkyl ether or a steroid derivative;

$R_2$ is independently selected at each occurrence to be absent, hydrogen, or optionally substituted lower alkyl;

$R_3$ is optionally substituted lower alkyl;

$R_4$ and $R_5$ are each independently chosen from the group consisting of optionally substituted alkylene, optionally substituted cycloalkylene, divalent neutral or charged hydrophilic moieties, and —$(CH_2CH_2O)_xCH_2CH_2$—;

$R_{10}$ and $R_{11}$ are each independently selected at each occurrence from the group consisting of hydrogen and optionally substituted lower alkyl groups;

x is an integer from about 1 to about 100;

$X^-$ is absent or is a counter ion, preferably a biocompatible anion, i.e., $X^-$ is present where the polymer comprises a charged group;

b is a positive integer, preferably b is an integer in the range of about 1 to about 20, about 1 to about 16, about 1 to about 12, about 1 to about 8 or about 1 to about 6; and n is an integer between about 5 and about 2,000.

Additionally preferred polymers according to formula V include polymers according to formula VI:

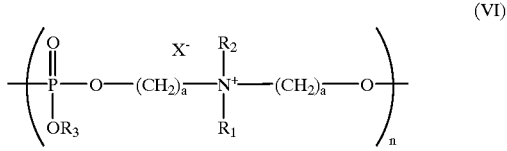
(VI)

wherein $R_2$ and $R_3$ are each independently selected optionally substituted lower alkyl groups;

$R_1$ is independently selected groups chosen at each occurrence from the group consisting of optionally substituted higher alkyl groups, poly(ethylene glycol) alkyl ether, and $(CR_{10}R_{11})_b$—Y—Z;

Y is —$OCO_2$— or —$NR_{10}CO_2$—;

Z is optionally substituted alkyl, poly(ethylene glycol) alkyl ether or a steroid derivative;

$R_{10}$ and $R_{11}$ are each independently selected at each occurrence from the group consisting of hydrogen, methyl and ethyl;

$X^-$ is absent or is a counter ion, preferably a biocompatible anion, i.e., $X^-$ is present where the polymer comprises a charged group;

a is an positive integer, preferably a is independently selected at each occurrence of a in the formula to be an integer from about 1 to about 20, from 1 to about 16, from 1 to about 12, from 1 to about 8, or from 1 to about 6;

b is a positive integer, preferably b is an integer in the range of about 1 to about 20, about 1 to about 16, about 1 to about 12, about 1 to about 8 or about 1 to about 6; and n is an integer between about 5 and about 2,000.

Preferred polymers of formula VI include $R_1$ groups according to formula VII:

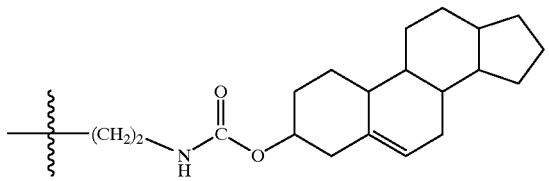
(VII)

wherein the steroid ring structure can optionally be substituted at one or more steroid ring atoms with one or more substitutents chosen from the group consisting of optionally substituted alkyl, optionally substituted alkenyl, optionally substituted alkynyl, and optionally substituted cycloalkyl and two or more substitutents can combine to form additional carbocyclic or heteroalicyclic rings which can be fused to the steroid ring system or can be spiro to the steroid ring system; or $R_1$ is —$(CH_2)_2NHCO_2$—R, wherein R is a straight chain alkyl group having from about 12 to about 24 carbon atoms.

It is understood in the Formulae as set forth above and below, the nitrogen positive charge ($^+$) is present only when the nitrogen is in a charged state, e.g., when $X^-$ is present.

As discussed above, the invention provides biodegradable nanoparticles including micelles. The micelles typically comprise one or more polymers having at least one phosphate group in the main chain of the polymer and the polymer having at least one positively charged group and at least one hydrophobic moiety. Typically micelles are composed of a polyphosphate of the invention having between about 1 or 5 and about 2,000 phosphate groups in the backbone and have a molecular weight of between about 500 or 1000 and 1,000,000. Suitable polyphosphates of the invention include those that have between about 10 and about 100, 200, 300, 400, 500, 600, 700, 800, 900, or 1000 phosphate groups in the polymer main chain and a molecular weight of between about 1,000 and about 50,000, 100,000, 200,000, 300,000, 400,000, 500,000, 600,000, 700,000, 800,000 or 900,000. Further, preferred micelles are composed of a polyphosphate of the invention have a net positive charge. Further, polyphosphate micelles of the invention self-aggregate into meso-stable phases such as lamellar or micellar phases.

The invention also provides biodegradable polymeric micelles comprising a biodegradable, amphiphilic polyphosphate having at least one phosphate group in the main chain of the polymer and the polymer preferably having at least one positively charged or positively chargeable group and at least one hydrophobic moiety. In preferred polymer micelles, the positively charged or positively chargeable groups are integral to the main chain of the polymer or are present in a phosphate side chain group. Further, the hydrophobic moieties are typically pendant from the polymer main chain and each hydrophobic group is linked to a phosphate group that is integral to the main chain.

In preferred embodiments, the biodegradable polymeric micelles of the invention are typically nanoparticles, particularly particles that have a diameter of about 50 nm to about 500 nm, more preferable are nanoparticles that have a diameter of between about 50 nm to about 400 nm, 300 nm, 200 nm or 100 nm and also preferred are nanoparticles that have a diameter of between about 50 nm, 100, nm, 200 nm, 300 nm, 400 nm to about 500 nm.

Preferred micelle or nanoparticles of the invention are capable of complexing, including or otherwise retaining one or more biologically active substances, particularly one or more neutral or negatively charged biologically active substances. Preferred negatively charged or neutral biologically active substances are selected from the group consisting of DNA (inclucive of cDNA), RNA (inclusive of mRNA, tRNA and other RNA's), proteins, and small molecule therapeutics.

Micelles suitable for use in the present invention include micelles comprised of a biodegradable polyphosphoester of Formula I, II, III, IV, V or VI. Preferably, the polyphosphate has a charge ratio of positive to negative charged groups that is greater than about 1.1, e.g., +/− ratio is greater than about 1.1/1, more preferred are polymers with a charge ratio of about 1.2 to about 3.0, of about 1.3, 1.4, 1.5, 1.6, 1.7, 1.8, 1.9, 2.0, 2.1, 2.2, 2.3, 2.4 or 2.5. Particularly preferred polyphosphates of the invention have a charge ratio of between about 1.5 and 2.0.

Preferred micelles and nanoparticles of the invention comprise at least one polyphosphate resin that comprises repeat units of the Formula (I):

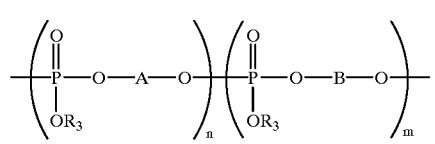
(I)

wherein

A and B can be the same or different and are each independently selected from the group consisting of optionally substituted alkylene, optionally substituted cyclic alkylene, optionally substituted arylene, optionally substituted heteroarylene, optionally substituted cyclic heteroalkylene, a hydrophilic divalent linker group, and $(CH_2CH_2O)_xCH_2CH_2$, such that A, B or both A and B comprise a positively charged or positively chargeable functional group in the mainchain and A, B or both A and B can be optionally substituted with one or more neutral or charged hydrophilic groups or hydrophobic groups;

x is an integer from about 1 to about 100;

$R_3$ is optionally substituted alkyl, optionally substituted aryl, optionally substituted heteroaryl, optionally substituted heteroalicyclic, optionally substituted cycloalkyl, optionally substituted aralkyl or optionally substituted cycloalkylalkyl; and each occurrence of $R_3$ can be optionally substituted with one or more neutral or charged groups or one or more hydrophobic moieties;

m and n are independently selected non-negative integers; and $m+n \geq 1$.

Preferred polymers of Formula I have the sum of m+n between about 5 and 2,000, more preferably between about 10 and 1,000 or between about 10 and 500. Also preferred are polymers of Formula I wherein x is between about 5 and 50 or between 5 and 20.

Additionally preferred micelles comprise at least one polymer according to Formula II:

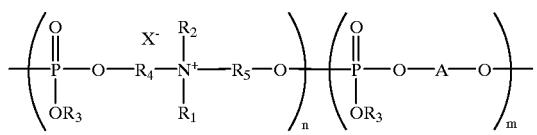

(II)

wherein $R_4$, $R_5$ and A are each independently chosen from the group consisting of optionally substituted alkylene, optionally substituted cycloalkylene, divalent neutral or charged hydrophilic moieties, $-(CH_2CH_2O)_xCH_2CH_2$;

x is an integer from 1 to about 100;

$R_1$ is hydrogen, optionally substituted alkyl, optionally substituted alkenyl, optionally substituted alkynyl, optionally substituted cycloalkyl, optionally substituted cycloalkylalkyl, optionally substituted aralkyl, optionally substituted heteroalicyclic, or $(CH_2)_a-Y-Z$ group wherein Y is an $-O-$, $-CO_2-$, $-NHCO_2-$, or $-OCO_2-$ functional group and Z is optionally substituted alkyl, optionally substituted alkenyl, optionally substituted alkynyl, optionally substituted cycloalkyl, optionally substituted cycloalkylalkyl, optionally substituted aralkyl, poly (ethylene glycol)-alkyl ether or a steroid derivative;

$R_2$ is independently selected at each occurrence to be absent, hydrogen, optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl; and $X^-$ is absent or is a counter ion, preferably a biocompatible anion.

Additionally preferred micelles comprise at least one polymer according to Formula III:

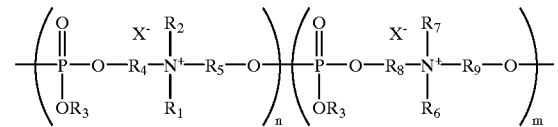

(III)

wherein $R_4$, $R_5$, $R_8$ and $R_9$ are independently selected at each occurrence from the group consisting of optionally substituted alkylene, optionally substituted cycloalkylene, and poly(ethyleneglycol) alkyl ether, each occurrence of $R_4$, $R_5$, $R_8$ and $R_9$ can be optionally substituted with a neutral or charged hydrophilic group selected from the group consisting of hydroxyl, hydroxyalkyl, aminoalkyl, N-alkyl aminoalkyl, N,N-dialkyl aminoalkyl, amino, N-alkylamino, N,N,dialkylamino, N,N,N-trialkylamino, amide, carboxylate, sulfate, phosphate and the like;

$R_2$ and $R_7$ are each independently selected groups chosen at each occurrence to be absent, hydrogen, optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl;

$R_3$ is independently selected at each occurrence to be optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl;

$R_1$ and $R_6$ are each independently selected groups chosen at each occurrence from the group consisting of hydrogen, optionally substituted alkyl, poly(ethylene glycol) alkyl ether, $(CR_{10}R_{11})_b-Y-Z$ wherein Y is $-OCO_2-$ or $-NR_{10}CO_2-$, Z is alkyl, poly(ethylene glycol) alkyl ether or a steroid derivative;

$R_{10}$ and $R_{11}$ are each independently selected at each occurrence from the group consisting of hydrogen and optionally substituted alkyl;

b is a positive integer, preferably b is an integer in the range of about 1 to about 20, about 1 to about 16, about 1 to about 12, about 1 to about 8 or about 1 to about 6;

$m+n \geq 1$; and $n \geq 1$.

Additionally preferred micelles comprise polymers according to Formula IV:

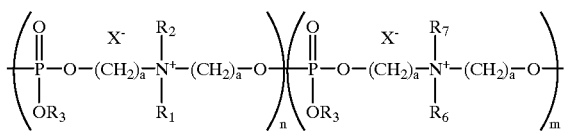

(IV)

wherein $R_2$ and $R_7$ are each independently selected to be absent, hydrogen or optionally substituted alkyl;

$R_1$ and $R_6$ are each independently selected at each occurrence to be hydrogen, optionally substituted higher alkyl or $(CH_2)_b-N(R_{10})CO_2-Z$;

$R_{10}$ is independently chosen at each occurrence to be hydrogen or optionally substituted lower alkyl groups;

Z is independently chosen at each occurrence of Z to be optionally substituted alkyl, $(CH_2CH_2O)_xCH_2CH_3$ or a steroid derivative;

a is an positive integer, preferably a is independently selected at each occurrence of a in the formula to be an integer from about 1 to about 20, from 1 to about 16, from 1 to about 12, from 1 to about 8, or from 1 to about 6;

b is a positive integer, preferably b is an integer in the range of about 1 to about 20, about 1 to about 16, about 1 to about 12, about 1 to about 8 or about 1 to about 6;

x is an integer from about 1 to about 100; and each $X^-$ is an independently selected counter ion, preferably a biocompatible anion.

Additionally preferred micelles comprise polymers according to Formula V:

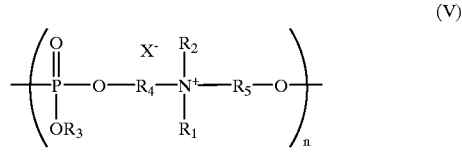

(V)

wherein $R_1$ is independently selected groups chosen at each occurrence from the group consisting of hydrogen, optionally substituted higher alkyl, poly(ethylene glycol) alkyl ether, and $-(CR_{10}R_{11})_b-Y-Z$ Y is $-OCO_2-$ or $-NR_{10}CO_2-$;

Z is optionally substituted alkyl, poly(ethylene glycol) alkyl ether or a steroid derivative;

$R_2$ is independently selected at each occurrence to be absent, hydrogen, or optionally substituted lower alkyl;

$R_3$ is optionally substituted lower alkyl;

$R_4$ and $R_5$ are each independently chosen from the group consisting of optionally substituted alkylene, cycloalkylene, divalent neutral or charged hydrophilic moieties, and $-(CH_2CH_2O)_xCH_2CH_2-$;

$R_{10}$ and $R_{11}$ are each independently selected at each occurrence from the group consisting of hydrogen and optionally substituted lower alkyl groups;

x is an integer from about 1 to about 100;

$X^-$ is absent or is a counter ion, preferably a biocompatible anion;

b is a positive integer, preferably b is an integer in the range of about 1 to about 20, about 1 to about 16, about 1 to about 12, about 1 to about 8 or about 1 to about 6; and n is an integer between about 5 and about 2,000.

Additionally preferred micelles comprising polyphosphates according to Formula V include micelles comprising polymers according to Formula VI:

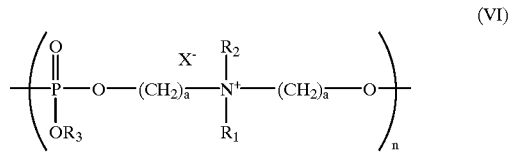

(VI)

wherein $R_2$ and $R_3$ are each independently selected optionally substituted lower alkyl groups;

$R_1$ is independently selected groups chosen at each occurrence from the group consisting of optionally substituted higher alkyl groups, poly(ethylene glycol) alkyl ether, and $(CR_{10}R_{11})_b-Y-Z$;

Y is $-OCO_2-$ or $-NR_{10}CO_2-$;

Z is optionally substituted alkyl, poly(ethylene glycol) alkyl ether or a steroid derivative;

$R_{10}$ and $R_{11}$ are each independently selected at each occurrence from the group consisting of hydrogen, methyl and ethyl;

$X^-$ is absent or is a counter ion, preferably a biocompatible anion;

a is an positive integer, preferably a is independently selected at each occurrence of a in the formula to be an integer from about 1 to about 20, from 1 to about 16, from 1 to about 12, from 1 to about 8, or from 1 to about 6;

b is a positive integer, preferably b is an integer in the range of about 1 to about 20, about 1 to about 16, about 1 to about 12, about 1 to about 8 or about 1 to about 6; and n is an integer between about 5 and about 2,000.

Additionally preferred are micelles comprising polyphosphates according to Formula V wherein $R_1$ is a group according to the Formula VII:

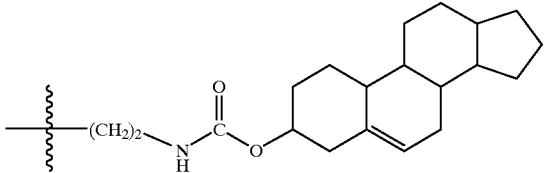

(VII)

wherein the steroid ring structure can optionally be substituted at one or more steroid ring atoms with one or more substitutents chosen from the group consisting of optionally substituted alkyl, optionally substituted alkenyl, optionally substituted alkynyl, and optionally substituted cycloalkyl and two or more substitutents can combine to form additional carbocyclic or heteroalicyclic rings which can be fused to the steroid ring system or can be spiro to the steroid ring system; or $R_1$ is $-(CH_2)_2NHCO_2-R$, wherein R is a straight chain alkyl group having from about 12 to about 24 carbon atoms.

Additionally preferred are micelles and other nanoparticles comprising at least on biodegradable amphiphilic polyphosphate according to Formula I, II, III, IV, V, or VI and at least one negatively charged or neutral biologically active substance. Preferred biologically active substances include DNA (inclusive of cDNA), RNA (inclusive of mRNA, tRNA and the like), proteins, and small molecule therapeutics.

The invention further includes a method of preparing a biodegradable amphiphilic polyphosphate having at least one phosphate group in the main chain of the polymer and the polymer having at least one positively charged group and at least one hydrophobic moiety, the method comprising the steps of:

providing at least one diol monomer and at least one phosphate precursor monomer; and reacting the diol monomer(s) and phosphate precursor monomer(s) under conditions conducive to the formation of a biodegradable amphiphilic polyphosphate.

A preferred method of preparing polyphosphates of the invention include polycondensation polymerization reactions wherein the diol monomer(s) and phosphate precursor (s) react via condensation reactions to form phosphate linkages.

In a particularly preferred method of preparing a biodegradable amphiphilic polyphosphate, the method comprises the steps of:

providing diol monomers, HO—A—OH and HO—B—OH, and a phosphate precursor $(R_3O)(Hal)_2P=O$, wherein A and B can be the same or different and are each independently selected from the group consisting of optionally substituted alkylene, optionally substituted cyclic alkylene, optionally substituted arylene, optionally substituted heteroarylene, optionally substituted cyclic heteroalkylene, a hydrophilic divalent linker group, and $(CH_2CH_2O)_xCH_2CH_2$, such that A, B or both A and B comprise a positively chargeable functional group in the mainchain and A, B or both A and B can be optionally substituted with one or more neutral or charged hydrophilic groups or hydrophobic groups;

$R_3$ is optionally substituted alkyl, optionally substituted aryl, optionally substituted heteroaryl, optionally substituted heteroalicyclic, optionally substituted cycloalkyl, optionally substituted aralkyl or optionally substituted cycloalkylalkyl; and each occurrence of $R_3$ can be optionally substituted with one or more neutral or charged groups or one or more hydrophobic moieties; and Hal is chloride, bromide, iodide or sulfonate;

reacting the diol monomers with the phosphate precursors under conditions conducive to a polycondensation polymerization reaction to generate a biodegradable amphiphilic polyphosphate of the Formula I.

In preferred embodiments, a polymer according to Formula II can be prepared by a method wherein the diol monomer HO—B—OH is a monomer of the Formula:

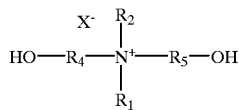

wherein $R_4$ and $R_5$ are each independently chosen from the group consisting of optionally substituted alkylene, optionally substituted cycloalkylene, divalent neutral or charged hydrophilic moieties, —$(CH_2CH_2O)_xCH_2CH_2$—;

x is an integer from 1 to about 100;

$R_1$ and $R_2$ are each independently chosen to be optionally substituted alkyl, optionally substituted alkenyl, optionally substituted alkynyl, optionally substituted cycloalkyl, optionally substituted cycloalkylalkyl, optionally substituted aralkyl, optionally substituted heteroalicyclic, or $(CH_2)_b$—Y-Z group;

Y is an —O—, —$CO_2$—, —$NHCO_2$—, or —$OCO_2$— functional group;

Z is optionally substituted alkyl, optionally substituted alkenyl, optionally substituted alkynyl, optionally substituted cycloalkyl, optionally substituted cycloalkylalkyl, optionally substituted aralkyl, poly(ethylene glycol)-alkyl ether or a steroid derivative;

b is a positive integer, preferably b is an integer in the range of about 1 to about 20, about 1 to about 16, about 1 to about 12, about 1 to about 8 or about 1 to about 6; and $X^-$ is absent or is a counter ion, preferably a biocompatible anion.

In other preferred embodiments, a polymer according to Formula III can be prepared by a method wherein the diol monomer, HO—B—OH is a monomer of the formula:

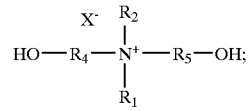

and diol monomer HO—A—OH is a monomer of the formula

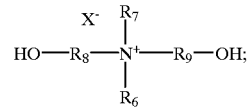

wherein $R_4$, $R_5$, $R_8$ and $R_9$ are independently selected at each occurrence from the group consisting of optionally substituted alkylene, optionally substituted cycloalkylene, and poly(ethyleneglycol) alkyl ether, each occurrence of $R_4$, $R_5$, $R_8$ and $R_9$ can be optionally substituted with a neutral or charged hydrophilic group selected from the group consisting of hydroxyl, hydroxyalkyl, aminoalkyl, N-alkyl aminoalkyl, N,N-dialkyl aminoalkyl, amino, N-alkylamino, N,N,dialkylamino, N,N,N-trialkylamino, amide, carboxylate, sulfate, phosphate poly(ethylene glycol), poly (ethylene glycol) alkyl ether, heteroaryl, optionally substituted imidazolyl, optionally substituted pyrazole; optionally substituted oxazoline and the like;

$R_2$, $R_3$ and $R_7$ are each independently selected groups chosen at each occurrence from the group consisting of optionally substituted alkyl, optionally substituted alkenyl, optionally substituted alkynyl, optionally substituted cycloalkyl, optionally substituted heteroalicyclic, optionally substituted aralkyl, and optionally substituted cycloalkylalkyl;

$R_1$ and $R_6$ are each independently selected groups chosen at each occurrence from the group consisting of optionally substituted alkyl, poly(ethylene glycol) alkyl ether, and $(CR_{10}R_{11})_b$—Y—Z;

Y is —$OCO_2$— or —$NR_{10}CO_2$—;

Z is optionally substituted alkyl, poly(ethylene glycol) alkyl ether or a steroid derivative;

$R_{10}$ and $R_{11}$ are each independently selected at each occurrence from the group consisting of hydrogen and optionally substituted alkyl; and b is a positive integer, preferably b is an integer in the range of about 1 to about 20, about 1 to about 16, about 1 to about 12, about 1 to about 8 or about 1 to about 6.

In preferred embodiments, the method of preparing a polyphosphate of the invention comprises the steps of:

providing a phosphate precursor, $(R_3O)(Hal)_2P=O$, and a diol monomer of the formula:

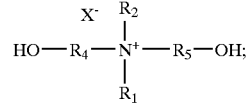

and reacting the diol monomer and the phosphate precursor under conditions conducive to the formation of a biodegradable polymer of the Formula V.

The present invention further provides methods of preparing a biodegradable amphiphilic polyphosphate micelle, the method comprising the steps of:

providing a biodegradable amphiphilic polyphosphate having at least one phosphate group in the main chain of the polymer and the polymer having at least one positively charged group and at least one hydrophobic moiety; and agitating a colloidal suspension of the polymer in a biphasic solution to obtain micelles having a diameter of between about 50 nm and 500 nm.

The present invention further provides methods of preparing a biodegradable micelle composition comprising a biodegradable amphiphilic polyphosphate micelle and a biologically active substance, the method comprising the steps of:

providing at least one biodegradable amphiphilic polyphosphate micelle and at least one biologically active substance; and contacting the micelle with the biologically active substance under conditions conducive to the inclusion of at least a portion of the biologically active substances into the micelles resulting in a biodegradable micelle composition comprising a biologically active substance.

The present invention further provides methods for the controlled release of a biologically active substance comprising the steps of:

providing a biodegradable amphiphilic polyphosphate micelle composition comprising:

(a) at least one biologically active substance; and (b) a biodegradable amphiphilic polyphosphate micelle having at least one phosphate group in the main chain of the polymer and the polymer having at least one positively charged group and at least one hydrophobic moiety;

contacting the micelle composition in vivo or in vitro with a biological fluid, cell or tissue under conditions conducive to the delivery of at least a portion of the biologically active substance to the biological fluid, cell or tissue so that the biologically active substance is released in a controlled manner.

Preferred methods for the controlled release of at least a portion of the biologically active substance from a micelle of the invention include methods wherein the biologically active substance is released either in vivo or in vitro. The invention also provides methods wherein the biologically active substance is released extracellularly or intracellularly.

Methods for the controlled localized release of a biologically active substance to a tissue or cell includes the use of a nanoparticle or micelle comprising at least one biodegradable polymer of the invention including at least one biodegradable polymer according to any one of Formula I, II, III, IV, V, VI or VII wherein the polymer has between about 5 and 2000 phosphate groups and the polymer has a molecular weight of between about 1000 and 1,000,000. Additionally preferred methods include the use of micelles or nanoparticle compositions which comprise a biologically active substance such as DNA, RNA, proteins, and small molecule therapeutics which is complexed or otherwise included within the polymer micelle or nanoparticle.

The present invention further provides methods for the controlled release of a biologically active substance wherein the biologically active substance is released from a micelle or other nanoparticle comprising at least one biodegradable amphiphilic polyphosphate according to Formula I, II, III, IV, V or VI.

Preferred polymers of the invention including polymers of Formula I, II, III, IV, V or VI have the sum of m+n between about 1 or 5 and 2,000, more preferably between about 10 and 1,000 or between about 10 and 500. Also preferred are polymers of Formula I wherein x is between about 5 and 50 or between 5 and 20.

Additional preferred polymers of the invention including biodegradable polymers according to Formula I, II, III, IV, V or VI which are suitable for use in methods of the controlled localized release of one or more biologically active substances include polymers having an $R^1$ group according to Formula VII:

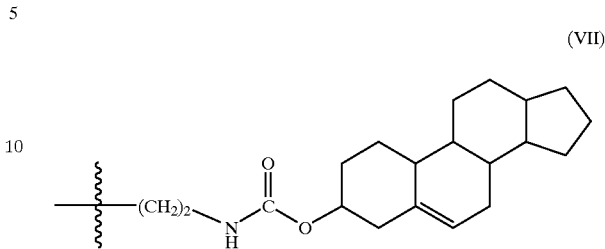

(VII)

wherein the steroid ring structure can optionally be substituted at one or more steroid ring atoms with one or more substitutents chosen from the group consisting of alkyl, alkenyl, alkynyl, and cycloalkyl and two or more substitutents can combine to form additional carbocyclic or heteroalicyclic rings which can be fused to the steroid ring system or can be spiro to the steroid ring system; or $R_1$ is —$(CH_2)_2NHCO_2$—R, wherein R is a straight chain alkyl group having from about 12 to about 24 carbon atoms.

The present invention also provides methods using biodegradable, amphiphilic polyphosphates of the invention and DNA or gene complexes thereof for gene therapy, the method comprising:

providing a biodegradable amphiphilic polyphosphate micelle composition comprising:

(a) at least a portion of at least one gene; and (b) a biodegradable amphiphilic polyphosphate micelle having at least one phosphate group in the main chain of the polymer and the polymer having at least one positively charged group and at least one hydrophobic moiety;

contacting the micelle composition in vivo or in vitro with a biological fluid, cell or tissue under conditions conducive to the delivery of at least a portion of the gene to the biological fluid, cell or tissue such that gene expression occurs.

Preferred methods for gene therapy include methods wherein the DNA sequence or gene is released either in vivo or in vitro. The invention also provides methods wherein the DNA sequence or gene is released extracellularly or intracellularly.

The present invention further provides methods for gene therapy wherein the DNA sequence or gene is released from a micelle or other nanoparticle comprising at least one polymer of the invention including at least one biodegradable amphiphilic polyphosphate according to any one of Formula I, II, III, IV, V or VI.

In preferred therapeutic and gene therapy methods of the invention, the method of administration of the micelle or nanoparticle composition comprising a biologically active substance is not particularly limited. However in certain preferred embodiments, micelles or other nanoparticles are administered orally or by injection into a tissue such as a muscle, an internal organ, a region of the spinal cord or the like. In a specific embodiment, a nanoparticle composition of the invention comprising a gene was administered by direct injection into a muscle of a mouse. More specifically, a polyphosphoester, PCEP, was used as a gene carrier for pLacZ plasmid. In vivo administration of the PCEP/pLacZ complex by injection into the tibialis muscle of BALB/C mice resulted in transfection of muscle cells. Gene expression was observed for several weeks at a dose of 5 µg DNA/leg. See FIG. 18 of the drawings, which shows that gene expression.

Suitable subjects for in vivo gene therapy using the compositions and methods of the invention are typically mammals. Particularly preferred mammals include rodents, including mice and rats, livestock such as sheep, pig, cow and the like and primates, particularly humans, however other subjects are also contemplated as within the scope of the present invention. Further, the compositions and methods of the present invention are also suitable for in vitro gene therapy applications.

The gene delivery systems of the present invention can achieve gene transfer efficiencies in vitro that are superior to commercially available cationic liposome preparations. Furthermore, these polymeric gene delivery systems offer numerous technical advantages including biodegradability of the gene delivery system, e.g., the polyphosphate nanoparticle or micelle can be degraded hydrolytically or enzymatically to biocompatible degradation products; stability of the gene delivery agent is improved relative to known liposome carriers; the versatility of polyphosphates of the invention which can be tailored by variation of one or more groups or substituents to control, charge density, charge ratio, polymer molecular weight, rate of degradation, hydrophilicity/hydrophobicity and other physical properties of the polymer and micelle; and specific cell or tissues can be targeted by introduction of one or more specific ligands into the polyphosphates of the invention thereby enhancing delivery of the biologically active substance to the specified location.

Nucleic acid administered in accordance with the invention may be any nucleic acid (DNA or RNA) including genomic DNA, cDNA, mRNA and tRNA. These constructs may encode a gene product of interest, e.g. a therapeutic or diagnostic agent. A wide variety of known polypeptides are known that may be suitably administered to a patient in accordance with the invention.

For instance, for administration to cardiac myocytes, nucleic acids that encode vasoactive factors may be employed to treat vasoconstriction or vasospasm. Nucleic acids that encode angiogenic growth factors may be employed to promote revascularization. Suitable angiogenic growth factors include e.g. the fibroblast growth factor (FGF) family, endothelial cell growth factor (ECGF) and vascular endothelial growth factor (VEGF; see U.S. Pat. Nos. 5,332,671 and 5,219,739). See Yanagisawa-Miwa et al., *Science* 1992, 257:1401–1403; Pu et al., *J Surg Res* 1993, 54:575–83; and Takeshita et al., *Circulation* 1994, 90:228–234. Additional agents that may be administered to ischemic heart conditions, or other ischemic organs include e.g. nucleic acids encoding transforming growth factor α (TGF-α), transforming growth factor β (TGF-β), tumor necrosis factor α and tumor necrosis factor β. Suitable vasoactive factors that can be administered in accordance with the invention include e.g. atrial natriuretic factor, platelet-derived growth factor, endothelin and the like.

For treatment of malignancies, particularly solid tumors, nucleic acids encoding various anticancer agents can be employed, such as nucleic acids that code for diphtheria toxin, thymidinekinase, pertussis toxin, cholera toxin and the like. Nucleic acids encoding antiangiogenic agents such as matrix metalloproteases and the like also can be employed. See J. M. Ray et al. *Eur Respir J* 1994, 7:2062–2072.

For other therapeutic applications, polypeptides transcribed by the administered nucleic acid can include growth factors or other regulatory proteins, a membrane receptor, a structural protein, an enzyme, a hormone and the like.

Also, as mentioned above, the invention provides for inhibiting expression or function of an endogenous gene of a subject. This can be accomplished by several alternative approaches. For example, antisense nucleic acid may be administered to a subject in accordance with the invention. Typically, such antisense nucleic acids will be complementary to the mRNA of the targeted endogenous gene to be suppressed, or to the nucleic acid that codes for the reverse complement of the endogenous gene. See J. H. Izant et al., *Science* 1985, 229:345–352; and L. J. Maher II et al., *Arch Biochem Biophys* 1987, 253:214–220. Antisense modulation of expression of a targeted endogenous gene can include antisense nucleic acid operably linked to gene regulatory sequences.

Alternatively, nucleic acid may be administered which antagonizes the expression of selected endogenous genes (e.g. ribozymes), or otherwise interferes with function of the endogenous gene or gene product.

The nucleic acid to be administered can be obtained by known methods, e.g. by isolating the nucleic acids from natural sources or by known synthetic methods such as the phosphate triester method. See, for example, Oligonucleotide Synthesis, IRL Press (M. J. Gait, ed. 1984). Synthetic oligonucleotides also may be prepared using commercially available automated oligonucleotide synthesizers. Also, as is known, if the nucleic acid to be administered is mRNA, it can be readily prepared from the corresponding DNA, e.g. utilizing phage RNA polymerases T3, T7 or SP6 to prepare mRNA from the DNA in the presence of ribonucleoside triphosphates. The nucleotide sequence of numerous therapeutic and diagnostic peptides including those discussed above are disclosed in the literature and computer databases (e.g., GenBank, EMBL and Swiss-Prot). Based on such information, a DNA segment may be chemically synthesized or may be obtained by other known routine procedures such as PCR.

To facilitate manipulation and handling of the nucleic acid to be administered, the nucleic acid is preferably inserted into a cassette where it is operably linked to a promoter. The promoter should be capable of driving expression in the desired cells. The selection of appropriate promoters can be readily accomplished. For some applications, a high expression promoter is preferred such as the 763-base pair cytomegalovirus (CMV) promoter. The Rous sarcoma (RSV) (Davis et al., *Hum Gene Ther,* 1993, 4:151) and MMT promoters also may be suitable. Additionally, certain proteins can be expressed using their native promoter. Promoters that are specific for selected cells also may be employed to limit transcription in desired cells. Other elements that can enhance expression also can be included such as an enhancer or a system that results in high expression levels such as a tat gene or a tar element. A cloning vehicle also may be designed with selective receptor binding and using the promoter to provide temporal or situational control of expression.

Typical subjects to which nucleic acid will be administered for therapeutic application include mammals, particularly primates, especially humans, and subjects for xenotransplant applications such as a primate or swine, especially pigs. For veterinary applications, a wide variety of subjects will be suitable, e.g. livestock such as cattle, sheep, goats, cows, swine and the like; poultry such as chickens, ducks, geese, turkeys and the like; and pets such as dogs and cats. For diagnostic or research applications, a wide variety of mammals will be suitable subjects including rodents (e.g. mice, rats, hamsters), rabbits, primates, and swine such as inbred pigs and the like.

The effective dose of nucleic acid will be a function of the particular expressed protein, the target tissue, the subject (including species, weight, sex, general health, etc.) and the subject's clinical condition. Optimal administration rates for a given protocol of administration can be readily ascertained by those skilled in the art using conventional dosage determination tests. Additionally, frequency of administration for a given therapy can vary, particularly with the time cells containing the exogenous nucleic acid continue to produce the desired polypeptide as will be appreciated by those skilled in the art. Also, in certain therapies, it may be desirable to employ two or more different proteins to optimize therapeutic results.

The concentration of nucleic acid within a polymer nanoparticle or micelle can vary, but relatively high concentrations are preferred to provide increased efficiency of nucleic acid uptake. More specifically, preferred nanoparticles and micelles comprise a polyphosphate-nucleic acid complex and includes between about 1% to 70% by weight of the nucleic acid. More preferably, the micelle or nanoparticle comprises about 10 to about 60% nucleic acid by weight or 10%, 20%, 30%, 40%, 50% or 60% by weight of the nucleic acid.

As indicated above, various substituents of the various Formulae are "optionally substituted", including $R_1$, $R_2$, $R_3$, $R_4$, $R_5$, $R_6$, $R_7$, $R_8$, $R_9$, $R_{10}$, and $R_{11}$ of Formula I–VII. When substituted, those substituents may be substituted by other than hydrogen at one or more available positions, typically 1 to about 6 positions or more typically 1 to about 3 or 4 positions, by one or more suitable groups such as those disclosed herein. Suitable groups that may be present on a "substituted" Ar, $R_1$, $R_2$, and $R_3$ group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an Ar group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

As used herein, the term "amphiphilic" is intended to include polymers which comprises two or more domains or groups which are linked together wherein at least one domain or group or domain is a polar, hydrophilic group and at least one domain or group is a non-polar hydrophobic group. Amphiphilic polymers of the invention typically comprise a polar, hydrophilic main chain having non-polar hydrophobic groups or domains pendant therefrom.

As used herein the term "main chain" is intended to have the standard polymer chemistry definition, e.g., the main chain refers the longest linear sequence of atoms in a polymer typically comprising the bonds or linkages that formed during the polymerization of monomers to form the polymer. For the polycarbonates of the instant invention, the main chain typically comprises the phosphate residues produced in the polymerization reaction.

As used herein, the term "a positively charged or positively chargeable group" is intended to include both positively charged functional groups such as phophonium groups, quaternary ammonium groups and other charged groups and also chargeable functional groups that can be reversibly protonated to yield a positively charged group, e.g., typical chargeable groups include primary, secondary and tertiary amines, amides and other functional groups which comprise a proton acceptor and can be protonated in aqueous media at or around neutral pH.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 36 carbon atoms. Typically lower alkyl groups have about 1 to about 20, 1 to about 12 or 1 to about 6 carbon atoms. Preferred lower alkyl groups are $C_1$–$C_{20}$ alkyl groups, more preferred are $C_{1-12}$-alkyl and $C_{1-6}$-alkyl groups. Especially preferred lower alkyl groups are methyl, ethyl, and propyl. Typically higher alkyl groups have about 4 to about 36, 8 to about 24 or 12 to about 18 carbon atoms. Preferred higher alkyl groups are $C_4$–$C_{36}$ alkyl groups, more preferred are $C_{8-24}$-alkyl and $C_{12-18}$-alkyl groups.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and about 20 carbon atoms and about 1 to about 8 heteroatoms, preferably about 1 to about 12 carbon atoms and about 1 to about 4 heteroatoms. Preferred heteroalkyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alylthio groups having 1, 2, 3, or 4 carbon atoms are particularly preferred. Prefered alkylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkylsulfinyl groups having 1, 2, 3, or 4 carbon atoms are particularly preferred. Preferred alkylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alylsulfonyl groups having 1, 2, 3, or 4 carbon atoms are particularly preferred. Preferred aminoalkyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkyl groups having 1, 2, 3, or 4 carbon atoms are particularly preferred.

As used herein, "heteroalkenyl" is intended to include branched, straight-chain and cyclic saturated aliphatic hydrocarbon groups including alkenylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkenylthio groups having 1, 2, 3, or 4 carbon atoms are particularly preferred. Prefered alkenylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkenylsulfinyl groups having 1, 2, 3, or 4 carbon atoms are particularly preferred. Preferred alkenylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkenylsulfonyl groups having 1, 2, 3, or 4 carbon atoms are particularly preferred. Preferred aminoalkenyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkenyl groups having 1, 2, 3, or 4 carbon atoms are particularly preferred.

As used herein, "heteroalkynyl" is intended to include branched, straight-chain and cyclic saturated aliphatic hydrocarbon groups including alkynylene, having the specified number of carbon atoms and at least one heteroatom, e.g., N, O or S. Heteroalkynyl groups will typically have between about 1 and about 20 carbon atoms and about 1 to about 8 heteroatoms, preferably about 1 to about 12 carbon atoms and about 1 to about 4 heteroatoms. Preferred heteroalkynyl groups include the following groups. Preferred alkynylthio groups include those groups having one or more thioether linkages and from 1 to about 12 carbon atoms, more preferably from 1 to about 8 carbon atoms, and still more preferably from 1 to about 6 carbon atoms. Alkynylthio groups having 1, 2, 3, or 4 carbon atoms are particularly preferred. Prefered alkynylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkynylsulfinyl groups having 1, 2, 3, or 4 carbon atoms are particularly preferred. Preferred alkynylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkynylsulfonyl groups having 1, 2, 3, or 4 carbon atoms are particularly preferred. Preferred aminoalkynyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkynyl groups having 1, 2, 3, or 4 carbon atoms are particularly preferred.

As used herein, "cycloalkyl" is intended to include saturated and partially unsaturated ring groups, having the specified number of carbon atoms, such as cyclopropyl, cyclobutyl, cyclopentyl, or cyclohexyl. Also included are carbocyclic ring groups with ine or more olefinic linkages between two or more ring carbon atoms such as cyclopentenyl, cyclohexenyl and the like. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylethyl.

As used here, "alkenyl" is intended to include hydrocarbon chains of straight, cyclic or branched configuration, including alkenylene having one or more unsaturated carbon-carbon bonds which may occur in any stable point along the chain, such as ethenyl and propenyl. Alkenyl groups typically have 1 to about 36 carbon atoms. Typically lower alkenyl groups have about 1 to about 20, 1 to about 12 or 1 to about 6 carbon atoms. Preferred lower alkenyl groups are $C_1$–$C_{20}$ alkenyl groups, more preferred are $C_{1-12}$-alkenyl and $C_{1-6}$-alkenyl groups. Especially preferred lower alkenyl groups are vinyl, and propenyl. Typically higher alkenyl groups have about 4 to about 36, 8 to about 24 or 12 to about 18 carbon atoms. Preferred higher alkenyl groups are $C_4$–$C_{36}$ alkenyl groups, more preferred are $C_{8-24}$-alkenyl and $C_{12-18}$-alkenyl groups.

As used herein, "alkynyl" is intended to include hydrocarbon chains of straight, cyclic or branched configuration, including alkynylene, and one or more triple carbon-carbon bonds which may occur in any stable point along the chain. Alkynyl groups typically have 1 to about 36 carbon atoms. Typically lower alkynyl groups have about 1 to about 20, 1 to about 12 or 1 to about 6 carbon atoms. Preferred lower alkynyl groups are $C_1$–$C_{20}$ alkynyl groups, more preferred are $C_{1-12}$-alkynyl and $C_{1-6}$-alkynyl groups. Especially preferred lower alkyl groups are ethynyl, and propynyl. Typically higher alkynyl groups have about 4 to about 36, 8 to about 24 or 12 to about 18 carbon atoms. Preferred higher alkynyl groups are $C_4$–$C_{36}$ alkynyl groups, more preferred are $C_{8-24}$-alkynyl and $C_{12-18}$-alkynyl groups.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 or 1 to about 6 carbon atoms.

As used herein, "a steroid derivative" is defined as an optionally substituted steroid group. A steroid is defined as a group of lipids that contain a hydrogenated cyclopentanoperhydrophenanthrene ring system. Some of the substances included in this group are progesterone, adrenocortical hormones, the gonadal hormones, cardiac aglycones, bile acids, sterols (such as cholesterol), toad poisons, saponins and some of the carcinogenic hydrocarbons. Preferred steroid derivatives include the sterol family of steroids, particularly cholesterol. Particularly preferred steroid derivatives include alkylene carboxamic acid steryl esters, e.g., -alkylene-NH—CO—O-steryl.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 or 1 to about 6 carbon atoms.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

As used herein, the term "aliphatic" refers to a linear, branched, cyclic alkane, alkene, or alkyne. Preferred aliphatic groups in the biodegradable amphiphilic polyphosphate of the invention are linear or branched and have from 1 to 36 carbon atoms. Preferred lower aliphatic groups have 1 to about 12 carbon atoms and preferred higher aliphatic groups have about 10 to about 24 carbon atoms.

As used herein, the term "aryl" refers to an unsaturated cyclic carbon compound with $4n+2\pi$ electrons where n is a non-negative integer, about 5–18 aromatic ring atoms and about 1 to about 3 aromatic rings.

As used herein, the terms "heterocyclic" and "heteroalicyclic" refer to a saturated or unsaturated ring compound having one or more atoms other than carbon in the ring, for example, nitrogen, oxygen or sulfur. Typical heterocyclic groups include heteroaromatic and heteroalicyclic groups that have about a total of 3 to 8 ring atoms and 1 to about 3 fused or separate rings and 1 to about 3 ring heteroatoms such as N, O or S atoms. Illustrative heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;- 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Biodegradable polymers differ from non-biodegradable polymers in that they can be degraded during in vivo or in vitro therapy. This generally involves breaking down the polymer into its monomeric subunits. In principle, the ultimate hydrolytic breakdown products of a polymer of the invention are one or more aliphatic alcohols or alkanediols, and phosphate. In certain embodiments, the ultimate hydrolytic breakdown products of a polymer according to Formulae III, IV or V may further comprise poly (ethyleneglycol) and other like biocompatible substances. All of these degradation products are potentially non-toxic. However, the intermediate oligomeric products of the hydrolysis may have different properties. Thus, toxicology of a biodegradable polymer intended for implantation or injection, even one synthesized from apparently innocuous monomeric structures, is typically determined after one or more toxicity analyses.

A typical in vitro toxicity assay would be performed with live cells, such as HeLa cells, according to the procedure outlined in Example 2 wherein polymers of the invention are evaluated using the stardard WST-1 dye reduction assay. HeLa cells seeded onto a multi well plate and incubated with 100 $\mu$L of DMEM medium complemented with 10% fetal bovine serum (FBS) containing a polymer of the invention. After culturing for 24–72 hours, ten microliters of WST-1 reagent (Boehringer Mannheim) was added to each well. After several hours, the absorbance of the supernatant at 450 m was measured against a 655 nm reference. Cytotoxicity of polymers was measured based on cell viability.

The polymer of the invention is preferably soluble in one or more common organic solvents for ease of fabrication and processing. Common organic solvents include such solvents as ethanol, chloroform, dichloromethane, acetone, ethyl acetate, DMAC, N-methyl pyrrolidone, dimethylformamide, and dimethylsulfoxide. The polymer is preferably soluble in at least one of the above solvents. Particularly preferred amphiphilic polyphospates are insoluble, sparingly soluble, or poorly soluble in aqueous media.

The polymer of the invention can also comprise additional biocompatible monomeric units so long as they do not interfere with the biodegradable characteristics desired. Such additional monomeric units may offer even greater flexibility in designing the precise release profile desired for targeted drug delivery, improved transfection of specified tissues or cells, or the precise rate of biodegradability desired for structural implants such as for therapeutic applications.

The process of the invention can take place at widely varying temperatures, depending upon whether a solvent is used and, if so, which one; the molecular weight desired; the susceptibility of the reactants to form side reactions; and the presence of an acid scavenger. Preferably, however, the process takes place at a temperature ranging from about −80° C. to about +200° C. Somewhat lower temperatures, e.g., for example from about −50 to about 100° C. may be possible with solution polymerization.

The time required for the process also can vary widely, depending on the type of reaction being used, the substitution pattern on the diol monomer(s), the type of phosphate precursor monomer being used, the molecular weight desired and, in general, the need to use more or less rigorous conditions for the reaction to proceed to the desired degree of completion. Typically, however, the process takes place during a time between about 30 minutes and 7 days.

While the process may be in bulk, in solution, by interfacial polycondensation, or any other convenient method of polymerization, preferably, the process takes place under solution conditions. Particularly useful solvents include methylene chloride, chloroform, tetrahydrofuran, dimethyl formamide, dimethyl sulfoxide or any of a wide variety of inert organic solvents.

Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

A polymer of the invention, e.g., a polymer of Formula I–VII can be isolated from the reaction mixture by conventional techniques, such as by precipitation, extraction, evaporation, filtration, crystallization and the like. Typically, however, the polymer of Formula I is both isolated and purified by addition of a non-solvent or a partial solvent, such as diethyl ether or petroleum ether to a polymerization reaction mixture thereby inducing precipitation of the polyphosphate.

The polymers of the invention are usually characterized by a release rate of the biologically active substance in vivo that is controlled at least in part as a function of hydrolysis of the phosphoester bond of the polymer during biodegradation. Additionally, the biologically active substance to be released may be conjugated to the phosphorus sidechain R' to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

Accordingly, the structure of the sidechain can influence the release behavior of compositions comprising a biologically active substance. For example, it is expected that conversion of the phosphate sidechain to a more lipophilic, more hydrophobic or bulky group would slow down the degradation process. Thus, release is usually faster from polymer compositions with a small aliphatic group sidechain than with a bulky aromatic sidechain.

The mechanical properties of the polymer are also important with respect to the processability in making molded or pressed articles for implantation. For example, the glass transition temperature can vary widely but must be sufficiently lower than the temperature of decomposition to accommodate conventional fabrication techniques, such as compression molding, extrusion or injection molding. The polymers of the invention typically have glass transition temperatures varying between about 25 to about 75° C. and, preferably, from about 45 to about 65° C.

Weight-average molecular weights (Mw) typically vary from about 2,000 to about 200,000 daltons, preferably from about 2,000 to about 100,000 daltons and, most preferably, from about 2,000 to about 20,000 daltons. Number average molecular weights (Mn) can also vary widely, but generally fall in the range of about 1,000 to 100,000, preferably about 1,000 to 50,000 and, most preferably, from about 1,000 to about 10,000. For controlled release of a substance from a polymer matrix applications, preferred polymers of the invention have a Mw that is directly proportional to the specified length of time over which polymer degradation occurs, e.g., high Mw polymers undergo complete degradation more slowly than low Mw polymers. Preferred polymers of the invention for use in tissue engineering applications and medical device applications, e.g., staples, scalpels and the like preferably have a high Mw and good mechanical properties.

Intrinsic viscosities generally vary from about 0.01 to about 2.0 dL/g in chloroform at 40° C., preferably from about 0.01 to about 1.0 dL/g and, most preferably, about 0.01 to about 0.5 dL/g.

A polymer of the invention including a polymer according to any one of Formula I, II, III, IV, V, or VI can be used either alone or as a composition containing, in addition, a biologically active substance to form a variety of useful biodegradable materials. For example, a polymer of the invention, including polymer according to any one of Formula I, II, III, IV, V or VI, can be used to produce nanoparticles including micelles and other mesophase structures, a biosorbable suture, an orthopedic appliance or bone cement for repairing injuries to bone or connective tissue, a laminate for degradable or non-degradable fabrics, or a coating for an implantable device, even without the presence of a biologically active substance.

Preferably, however, the biodegradable polymer composition comprises both:
(a) at least one biologically active substance and
(b) a polymer according to any one of Formula I, II, III, IV, V or VI.

Biologically active substances of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Preferred biologically active substances include negatively charged and neutral substances. Particularly preferred biologically active substances are DNA, RNA, proteins and negatively charged or neutral therapeutic small molecules.

Non-limiting examples of useful biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

Specific examples of useful biologically active substances from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, partricularly those useful in vaccine applications.

Preferably, the biologically active substance is selected from the group consisting of polysaccharides, growth factors, hormones, anti-angiogenesis factors, interferons or cytokines, DNA, RNA, proteins and pro-drugs. In a particularly preferred embodiment, the biologically active substance is a therapeutic drug or pro-drug, more preferably a drug selected from the group consisting of chemotherapeutic agents and other anti-neoplastics, antibiotics, anti-virals, anti-fungals, anti-inflammatories, anticoagulants, an antigenic materials. Particularly preferred biologically active substances are DNA and RNA sequences that are suitable for gene therapy.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include polycarbonates; polyesters; polyorthoesters; polyamides; polyurethanes; poly(iminocarbonates); and polyanhydrides.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

In its simplest form, a biodegradable therapeutic agent delivery system consists of a dispersion of the therapeutic agent in a polymer matrix. The therapeutic agent is typically released as the polymeric matrix biodegrades in vivo into soluble products that can be excreted from the body. Preferred delivery systems or biodegradable amphiphilic polyphosphate compositions include polyphosphates formed into nanoparticles. Nanoparticles are not particularly limited in shape or organization, however micelles and other polymer architectures which have regular mesophase organization, e.g., lamellar and other phases, are preferred.

In a preferred embodiment, the article of the invention is designed for implantation or injection into the body of an animal. It is particularly important that such an article result in minimal tissue irritation when implanted or injected into vasculated tissue.

As a drug delivery device, the polymer compositions of the invention provide a polymeric matrix capable of sequestering a biologically active substance and provide predictable, controlled delivery of the substance. The polymeric matrix then degrades to non-toxic residues.

In one embodiment, the invention provides biodegradable polymers prepared by polycondensation of ethyl phosphorodichloridate and a diol containing a cholesteryl side chain (structure shown in scheme 1) or a diol containing a straight chain hexadecyl side chain (structure shown in scheme 2). The synthetic route is shown in Schemes 3 and 4.

In another embodiment, the structure of the polymer is designed as shown in Scheme 1.

Scheme 1
Structure of PCEP

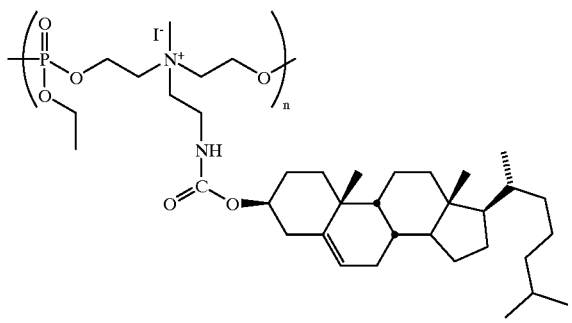

Scheme 2
Structure of PPEP

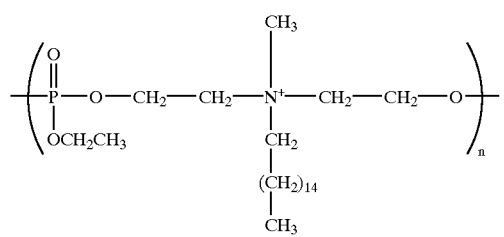

One skilled in the art will recognize that other related amphiphilic polymers can also be used in the present invention. In each case, two functional domains are essential for effective gene delivery, a cationic group either attached to a phosphate group of the main chain or incorporated into the backbone, and a hydrophobic moiety (membrane-interactive moiety) attached to the backbone. An additional hydrophilic group could also be incorporated into either the backbone or to the side chain, this hydrophilic moiety could be neutral or charged.

The following examples are offered by way of illustration and are not intended to limit the invention in any manner.

EXAMPLE 1

Synthesis and Characterization of PCEP-Poly{[(cholesteryl oxo-carbonylamido ethyl) methyl bis(ethylene) Ammonium Iodide] Ethyl Phosphate}

The synthesis of Poly{[(cholesteryl oxo-carbonylamido ethyl) methyl bis(ethylene) ammonium iodide] ethyl phosphate } (PCEP) is outlined in Scheme 3 and 4. Individual steps are discussed below.

Scheme 3
Synthesis of a diol monomer comprising a cholesterol derivative pendant from a quarternary ammonium center

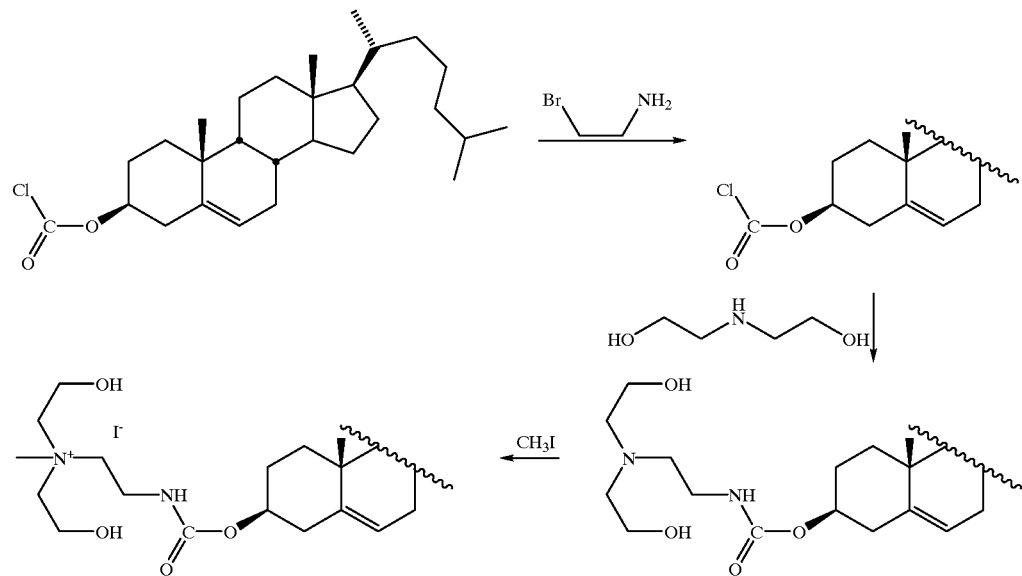

Scheme 4
Polymerization of a diol monomer with a phosphate precursor to form PCEP

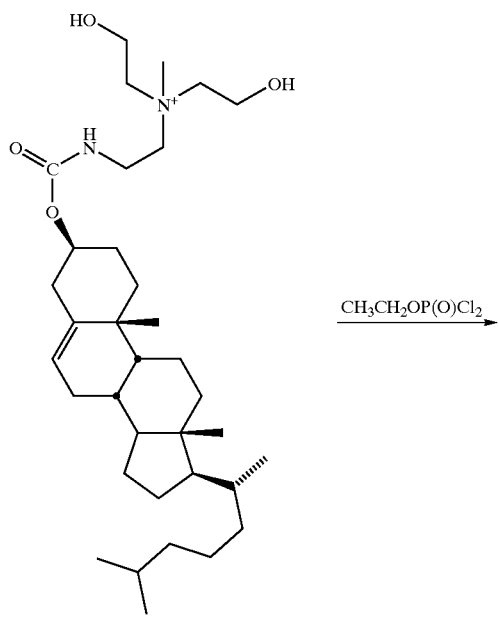

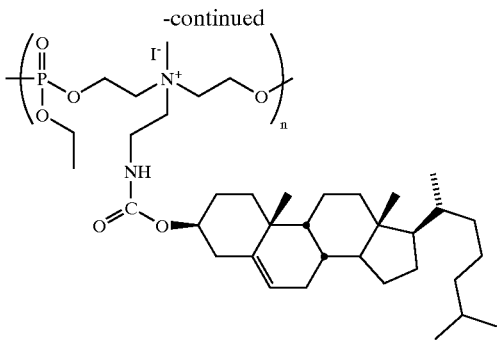

-continued

Cholesteryl (2-bromoethyl) carbamate (1):

To an ice-cooled mixture of 2-bromoethylamine hydrobromide (11.27 g, 55.0 mmol) in 80 ml dichloromethane was added 16 ml (11.62 g, 114.8 mmol) triethylamine, and cholesterol chloroformate (22.46 g, 50.0 mmol) in 80 ml dichloromethane. The mixture was stirred at room temperature overnight then filtered. The filtrate was washed with 0.1 M HCl/saturated NaCl (100 ml×3) and water (100 ml), dried over magnesium sulfate. The crude product was recrystallized from ethanol to give white powder (1) yield 73%, m.p. 113–115° C.

Cholesteryl (2-[bis(2-hydroxyethyl)-amino]ethyl) carbamate (2):

A mixture of cholesterol (2-bromoethyl)-carbamate (1) (15.83 g, 29.5 mmol), diethanolamine (3.11 g, 29.5 mmol), anhydrous potassium carbonate (10.0 g, 72.35 mmol) and 150 ml toluene was refluxed overnight. After cooling down, the mixture was filtered and the solid was washed with dichloromethane. The filtrate was concentrated and residue was recrystallized from bezene/hexane to give a white powder (2), yield 82%, m.p. 200–210° C. The structure of (2) was confirmed by its $^1$H-NMR spectrum (FIG. 1).

Cholesterol (2-[bis(2-hydroxyethyl)-ammnium]ethyl) carbamate iodide (3):

A mixture of (2) (12.52 g, 22.32 mmol) and iodomethane (1.8 ml, 28.91 mmol) in 150 ml methanol was refluxed overnight to give a clear solution. The solution was concentrated to a small volume, and five volumes of ether was added. The resulting white precipitate was collected and dried under vacuum, yield 97%, m.p. 225° C. (dec). The structure of (3) was confirmed by 1H-NMR spectrum (FIG. 2).

Poly-{[(cholesteryl oxocarbonylamido ethyl) methyl bis(ethylene) ammonium iodide] ethyl 2hosghate} (PCEP):

To a 25 ml chloroform solution containing 1.404 g of (3), 0.025 g DMAP and 0.404 g triethylamine, 0.326 g of ethyl dichlorophosphate in 10 ml chloroform was added dropwise at $0^-5°$ C. within 1 hr under stirring. The solution was then stirred at room temperature overnight. The reaction mixture was extracted with saturated NaCI solution containing small amount of sodium hydrosulfite for three times, and twice with water. The organic layer was dried over anhydrous sodium sulfate and concentrated. PCEP was precipitated after a large amount of ether was added. The polymer (PCEP) was collected and dried under vacuum. Yield 69%.

Structure characterization of PCEP.

The structure of PCEP was ascertained by $^1$H-NMR (FIG. 3). Gel permeation chromatography analysis (FIG. 4) indicated that PPEC synthesized by the above method has a molecular weight of 4020.

EXAMPLE 2

Assay For the Cytotoxicity of PCEP

Cytotoxicity of PCEP, cholesteryl (2-[bis(2-hydroxyethyl)-ammnium]ethyl) carbamate iodide (3) and other potential gene carriers (poly-L-lysine and LipofectAMINE) was evaluated using the WST-1 dye reduction assay. HeLa cells were seeded in a 96 well plate 24 hours before the assay at the density of $5\times10^4$ cells/well. The cells were incubated for 4 hours with 100 μL of DMEM medium complemented with 10% fetal bovine serum (FBS) containing PCEP, (3), poly-L-lysine or Lipofectarnine at different concentrations ranging from 0 to 100 μg/ml. The medium in each well was replaced with 100 μl of fresh complete medium and cells were cultured for an additional 20 hrs. Ten microliters of WST-1 reagent (Boehringer Mannheim) was added to each well and allowed to react for 4 hrs at 37° C. The absorbance of the supernatant at 450 nm (use 655 nm as a reference wavelength) was measured using a microplate reader (Model 550, Bio-Rad Lab. Hercules, Calif.).

The assay results (FIG. 5) indicated that PCEP exhibited much lower cytotoxicity in culture than widely used polycationic carrier, poly-L-lysine, and a standard in vitro transfection reagent LipofectAMINE. At a concentration of 60 μg/ml, HeLa cells in the PCEP group showed 75% viability, while the cell viability for LipofectAMINE is 42%, and 8% for poly-L-lysine. When comparing with the monomer (3), PCEP showed a reduced cytotoxicity.

EXAMPLE 3

Preparation and Characterization of PCEP Micelles and the PCEP-plasmid DNA Complex Preparation of PCEP-DNA complex:

PCEP was dissolved in chloroform at a concentration of 2–10 mg/ml in a round bottom flask, and a required volume of phosphate-buffered saline (PBS) was added, colloidal particles formed by followed by agitation and sonicated to obtain particles with a size below 200 rim. Chloroform was then evaporated using a rotary evaporator. The complex between PCEP and plasmid DNA formed upon mixing an appropriate amount of PCEP micelles and plasmid DNA. The complexes were used directly for the transfection study unless stated otherwise.

The size and the zeta potential of the polymeric micelles and the complexed micelles were determined by photon correlation spectroscopy and laser Doppler anemometry respectively using a Zetasizer® 3000 (Malvern Instruments Inc. Southborough, Mass.). The measurement was performed at 25° C. in PBS with a detection angle of 90°.

The amount of DNA complexed with PCEP was calculated by the difference between the total amount incorporated in the starting preparation buffer and the amount of non-entrapped DNA remaining in the aqueous suspension after the complexation process. Polymeric micelles suspension was centrifuged in a series 35%–55%–85% (w/v) sucrose gradients at 50,000×g for 20 min. The amount of DNA remain in the supernatant, accounted for the non-entrapped DNA, was analyzed using the Hoechst 33258 dye on a DyNA Quant™ 200 fluorometer (Hoefer Pharmacia Biotech Inc., San Francisco, Calif.).

Preparation of PCEP-DNA complex with chloroquine sulfate (CQ):

Chloroquine sulfate (CQ) has been widely proven to be an effective reagent to disrupt lysosomes and enhance the transfection efficiency in many polycationic gene delivery systems. CQ was co-encapsulated into the nanoparticles simply by incorporating CQ into the preparation solutions. The CQ incorporated micelles were used for in vitro transfection without further purification since the total amount of CQ added is still within the non-toxic concentration range.

Characterization of PCEP micelles and PCEP-DNA complexes:

The volume average size of PCEP micelles ranged from 150–200 nm, with a very narrow distribution. A typical size report was shown in FIG. 6.

The optimal concentrations of PCEP and plasmid DNA to form the complexes were examined at room temperature in PBS. FIG. 7 showed the effect of charge ratio or weight ratio of PCEP/DNA on the size of the complexes estimated by phase-contrast microscopy observation. At a charge ratio below 2.5 and above 4.2, the size of the complexes was below 1 μm. In between, complex aggregated to a size roughly 10 μm. FIG. 8 was a report on the size of a typical batch of complexes prepared at a +/− charge ratio of 1.5. The average size of complexes was 160 nm, slightly larger than the PCEP micelles. However, the distribution is much wider. The surface charge reduced slightly. This is probably due to the large access of PCEP micelles.

There was no significant difference in size and Zeta potential between the complexes with CQ incorporated and the ones without.

The formation of PCEP-DNA complexes was examined by their electrophoretic mobility on an agarose gel at various charge ratios of PCEP micelles to plasmid DNA (FIG. 9). No migration of the plasmid DNA occurred at charge ratio larger than 1.5. This lack of migration was due to neutralization of the nucleic acid by PCEP, suggesting the polycationic nature of PCEP.

EXAMPLE 4

Transfection Efficiency of PCEP-DNA Complex in Different Cell Lines

In vitro transfection of HEK 293 cells with complexes of PCEP and pRE-Luciferase DNA:

Cells were seeded 24 hours prior to transfection into a 12-well plate (Becton-Dickinson, Lincoln Park, N.J. at a density of 8×10⁴ per well with 1 ml of complete medium (DMEM containing 10% FBS, supplemented with 2 mM L-glutamate, 50 units/ml penicillin and 50 μg/ml streptomycin). At the time of transfection, the medium in each well was replaced with 0.5 ml of Opti-MEM or DMEM-1% FBS medium. PCEP-DNA complexes or LipofectAMINET™-DNA complexes were incubated with the cells for 4 hours at 37° C. Then the medium was replaced with 1 ml of fresh complete medium and cells were further incubated for 72 hours. All the transfection tests were performed in triplicate. The transfection efficiency was evaluated using one of the following three assay methods depending on the gene used in the transfection experiments. After the incubation, cells were permeabilized with 100 μL of cell lysis buffer (Promega Co., Madison, Wis.). The luciferase activity in cell extracts was measured using a luciferase assay kit (Promega. Co., Madison, Wis.) on a luminometer (Analytical Luminescence Lab, San Diego, Calif.). The light units (LU) were normalized against protein concentration in the cell extracts, which was measured using a protein assay kit (Bio-Rad Labs, Hercules, Calif.).

Chloroquine loaded nanoparticles

Chloroquine (CQ) has been widely proven to be an effective reagent to disrupt lysosomes and enhance the transfection efficiency in many polycationic gene delivery systems. CQ was coencapsulated into the complexes simply by incorporating CQ with plasmid DNA or with PCEP micelles during the complexation. The effects of CQ and medium composition on the transfection results were first examined. FIG. 10 showed the transfection efficiency of PCEP-DNA complexes prepared in Opti-MEM and deionized water when the transfection was performed in either Opti-MEM or DMEM-1%FBS. The transfection efficiency of CQ loaded complexes was also shown. The highest gene expression was obtained by using CQ incorporated complexes in Opti-MEM. A dose response study on CQ effect (FIG. 11) showed that the transfection reached the maximum level at a concentration level of 75 μM for CQ. The mixing sequence of CQ with PCEP and plasmid DNA affects the transfection efficiency (FIG. 13). Incubating CQ with DNA first before complexed with PCEP micelles resulted in twice as much as luciferase expression than if CQ was incubated with PCEP before complexed with pcDNA. This suggested that CQ be incorporated into the PCEP-DNA complexes although the incorporation efficiency was not measured. In the following studies, all the PCEP-DNA complexes were prepared in Opti-MEM. CQ was, incorporated in the complexes as in Protocol 2 (FIG. 12), and the transfection was performed in Opti-MEM, unless otherwise stated.

As the gel electrophoresis analysis shown, at a +/− charge ratio of 1.5 and above, all the plasmid DNA added to the preparation mixture was complexed with PCEP micelles. Complexes prepared at different charge ratios were examined for their abilities to transfect HEK293 cells (FIG. 13). The highest level of gene transfection was observed when the complexes were synthesized at the +/− charge ration between 1.5 and 2.0. No significant difference was detected between the complexes prepared at +/− ratio of 1.5 and 2.0. The transfection efficiency decreased as the +/− increased.

The gene expression as a function of dose was evaluated in HEK293 cells. The +/− charge ratio was fixed at 2.0. The luciferase expression level increased with the dose, reaching the maximum level of 8.5×10⁸ LU/min/mg protein at a dose of 4 μg DNA/well (FIG. 14). The average gene expression level decreased at a dose of 10 μg of DNA/well, although the mechanism is unknown. The PCEP concentration is still far below its toxic level (FIG. 5). However the difference between the 4 μg of DNA dose and 10 μg of DNA was not statistically significant. The transfection performed in DMEM-1% FBS showed the similar trend.

In vitro transfection of other cell lines with PCEP-DNA complexes:

The transfection efficiency was measured against two other cell lines using PCEP-DNA complexes containing pRE-Luciferase plasmid (FIGS. 15 and 16). Transfections on HeLa cells and CaCO-2 cells were corned out according to the same protocol described above.

Like in HEK293 cells, the highest level of luciferase expression in HeLa cells was also found to be at a +/− ratio of 1.5 to 2.0 (FIG. 15). The transfection performed in Opti-MEM medium with the complexes prepared in the same medium gave much higher (over two orders of magnitudes higher) levels of gene expression than that in deionized water at the same charge ratios. The transfection efficiency in CaCO-2 cells (FIG. 16), although about 10 times lower than that of LipofectAMINE transfection, was more than four orders of magnitudes higher than the background.

EXAMPLE 5

The Storage Stability of PCEP-DNA Complex

Storage stability and reproducibility were also some of the essential issues to the success of gene therapy. The simplicity of the PCEP-DNA complex preparation allowed the process to be reproduced. PCEP-DNA complexes were stored at room temperature for three days and were used to transfect HEK293 cells along with the freshly prepared complexes (FIG. 17). The transfection efficiency of the complexes was about five times lower after three days storage at room temperature. Interestingly, the complexes froze at −20° C. for three days showed an even slightly lower gene expression level.

Via structural design, polymeric micelles with better stability could be synthesized and higher stability of polymer-DNA complex formulations could be achieved.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A biodegradable polyphosphate having at least one phosphate group in the main chain of the polymer and the polymer having at least one positively charged or positively chargeable group and at least one hydrophobic moiety, wherein the polymer comprises repeat units of the formula:

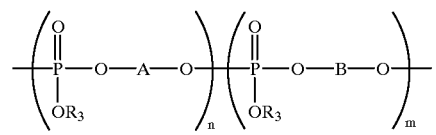

wherein

A and B can be the same or different and are each independently selected from the group consisting of $C_{1-20}$alkylene, $C_{3-20}$cyclic alkylene, $C_{5-20}$arylene, $C_{5-20}$heteroarylene, $C_{3-20}$cyclic heteroalkylene, a hydrophilic divalent linker group, and $(CH_2CH_2O)_xCH_2CH_2$, such that A, B or both A and B comprise a positively charged or positively chargeable functional group in the mainchain and A, B or both A and B can be optionally substituted with one or more neutral or charged hydrophilic groups or hydrophobic groups:

$R_3$ is $C_{1-20}$alkyl, $C_{5-20}$aryl, $C_{5-20}$heteroaryl, $C_{3-8}$heteroalicyclic, $C_{3-8}$cycloalkyl, $C_{3-20}$aralkyl or $C_{3-8}$cycloalkyl $C_{1-20}$alkyl; and each occurence of $R_3$ can be optionally substituted with one or more neutral or charged groups or one or more hydrophobic moieties;

x is an integer between about 1 and about 100;

m and n are independently selected non-negative integers; and m+n>1.

2. A polymer of claim 1, wherein the polymer is amphiphilic.

3. A polymer of claim 1, wherein the polymer has a net positive charge.

4. A polymer of claim 1, wherein the polymer is biocompatible before, during and upon biodegradation.

5. A polymer of claim 1, wherein the positively charged groups are integral to the main chain of the polymer or are present in a phosphate side chain group.

6. A polymer of claim 1, wherein the hydrophobic moieties are groups pendant from the polymer main chain and each hydrophobic group is linked to a phosphate group or a charged group that is integral to the main-chain of the polymer.

7. A polymer of claim 1 further comprising a hydrophilic group which can be neutral or charged, the hydrophilic group either can be integral to the polymer main chain or can be a pendant group that is linked to the main chain.

8. A polymer of claim 1, wherein the biodegradable polymer has between about 5 and about 2,000 phosphate groups in the backbone.

9. A polymer of claim 1, wherein the biodegradable polymer has a molecular weight of between about 1000 and 1,000,000.

10. A polymer of claim 1, wherein the polymer comprises repeat units according to the formula:

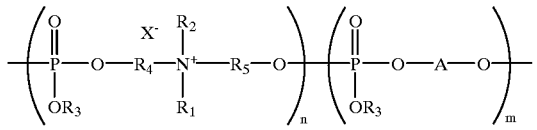

wherein $R_4$, $R_5$ and A are each independently chosen from the group consisting of $C_{1-20}$alkylene, $C_{3-20}$cycloalkylene, divalent neutral or charged hydrophilic moieties, $-(CH_2CH_2O)_xCH_2CH_2-$;

x is an integer from 1 to about 100;

$R_1$ is hydrogen, $C_{1-36}$alkyl, $C_{2-36}$alkenyl, $C_{2-36}$alkynyl, $C_{3-20}$cycloalkyl, $C_{3-8}$cycloalkyl$C_{1-36}$alkyl, $C_{7-18}$aralkyl, $C_{3-20}$heteroalicyclic, or $(CH_2)_m-Y-Z$ group;

Y is an $-O-$, $-CO_2-$, $-NHCO_2-$, or $-OCO_2-$ functional group;

Z is $C_{1-36}$alkyl, $C_{2-36}$alkenyl, $C_{2-36}$alkynyl, $C_{3-20}$cycloalkyl, $C_{3-8}$cycloalkyl$C_{1-36}$alkyl, $C_{7-18}$aralkyl, poly(ethylene glycol)-$C_{1-36}$alkyl ether or a steroid derivative;

$R_2$ is absent, hydrogen, $C_{1-36}$alkyl, $C_{3-20}$cycloalkyl, $C_{3-20}$heteroalicyclic, $C_{7-18}$aralkyl, or $C_{3-8}$cycloalkyl $C_{1-36}$alkyl; and $X^-$ is a biocompatible anion.

11. A polymer of claim 10, wherein the polymer comprises repeat units according to the formula:

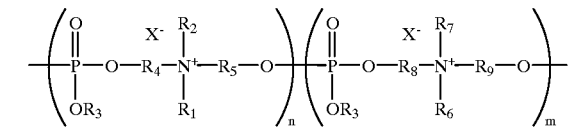

wherein $R_4$, $R_5$, $R_8$ and $R_9$ are independently selected at each occurrence from the group consisting of $C_{1-36}$alkylene, $C_{5-36}$cycloalkylene, and poly(ethyleneglycol) alkyl ether, each occurrence of $R_4$, $R_5$, $R_8$ and $R_9$ can be optionally substituted with a neutral or charged hydrophilic group selected from the group consisting of hydroxyl, hydroxy $C_{1-8}$alkyl, amino $C_{1-8}$alkyl, N—$C_{1-8}$alkyl amino $C_{1-8}$alkyl, N,N-di $C_{1-8}$alkyl amino $C_{1-8}$alkyl, amino, N—$C_{1-8}$alkylamino, N,N,di $C_{1-8}$alkylamino, N,N,N-tri $C_{1-8}$alkylamino, amide, carboxylate, sulfate, and phosphate;

$R_2$ and $R_7$ are each independently at each occurrence either absent or are selected from the group consisting of hydrogen, $C_{1-36}$alkyl, $C_{3-20}$cycloalkyl, $C_{3-20}$heteroalicyclic, $C_{7-18}$aralkyl, and $C_{3-8}$cycloalkyl $C_{1-36}$alkyl;

$R_3$ is $C_{1-36}$alkyl, $C_{3-20}$cycloalkyl, $C_{3-20}$heteroalicyclic, $C_{7-18}$aralkyl, or $C_{3-8}$cycloalkyl $C_{1-36}$alkyl;

$R_1$ and $R_6$ are each independently selected groups chosen at each occurrence from the group consisting of hydrogen, $C_{1-36}$alkyl, poly(ethylene glycol) alkyl ether, $(CR_{10}R_{11})_b-Y-Z$;

Y is $-OCO_2-$ or $-NR_{10}CO_2-$;

Z is alkyl poly(ethylene glycol) alkyl ether or a steroid derivative;

$R_{10}$ and $R_{11}$ are each independently selected at each occurrence from the group consisting of hydrogen and $C_{1-6}$alkyl;

b is a positive integer;

m+n≧1; and n≧1.

12. A polymer of claim 10, wherein the polymer comprises repeat units according to the formula:

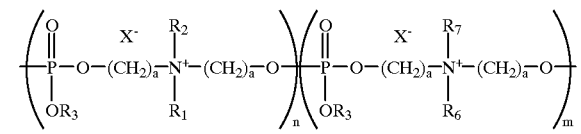

wherein $R_2$ and $R_7$ are each independently selected at each occurrence to be absent, hydrogen or $C_{1-20}$alkyl;

$R_1$ and $R_6$ are each independently selected at each occurrence to be hydrogen, $C_{1-36}$alkyl or $(CH_2)_b-N(R_{10})CO_2-Z$;

$R_{10}$ is independently chosen at each occurrence to be hydrogen or $C_{1-6}$alkyl;

Z is independently chosen at each occurrence of Z to be alkyl, $(CH_2CH_2O)_xCH_2CH_3$ or a steroid derivative;

a is an positive integer;

b is a positive integer; and x is an integer from about 1 to about 20.

13. A polymer of claim 1, wherein the polymer comprises repeat units according to the formula:

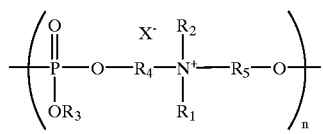

wherein $R_1$ is independently selected groups chosen at each occurrence from the group consisting of hydrogen, $C_{1-36}$alkyl, poly(ethylene glycol) alkyl ether, $(CR_{10}R_{11})_b$—Y—Z;

Y is —OCO$_2$— or —NR$_{10}$CO$_2$—;

Z is $C_{1-36}$alkyl, poly(ethylene glycol) alkyl ether or a steroid derivative;

$R_2$ is independently selected at each occurrence to be absent, hydrogen, or a $C_{1-36}$alkyl;

$R_3$ is $C_{1-36}$alkyl;

$R_4$ and $R_5$ are each independently chosen from the group consisting of $C_{1-36}$alkylene, $C_{3-36}$cycloalkylene, divalent neutral or charged hydrophilic moieties, —(CH$_2$CH$_2$O)$_x$CH$_2$CH$_2$;

$R_{10}$ and $R_{11}$ are each independently selected at each occurrence from the group consisting of hydrogen and $C_{1-6}$alkyl;

x is an integer from about 1 to about 100;

$X^-$ is a biocompatible anion;

b is a positive integer; and n is an integer between about 5 and about 2,000.

14. A polymer of claim 13, wherein the polymer comprises repeat units according to the formula:

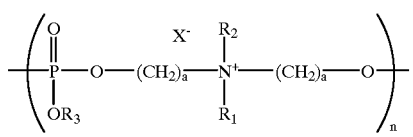

wherein $R_2$ and $R_3$ are each independently selected $C_{1-6}$alkyl groups;

$R_1$ is independently selected groups chosen at each occurrence from the group consisting of $C_{8-24}$alkyl, poly(ethylene glycol) alkyl ether, $(CR_{10}R_{11})_b$—Y—Z;

Y is —OCO$_2$— or —NR$_{10}$CO$_2$—;

Z is $C_{1-36}$alkyl, poly(ethylene glycol) alkyl ether or a steroid derivative;

$R_{10}$ and $R_{11}$ are each independently selected at each occurrence from the group consisting of hydrogen, methyl and ethyl;

$X^-$ is a biocompatible anion;

a is an positive integer;

b is a positive integer; and n is an integer between about 5 and about 2,000.

15. A polymer of claim 14, wherein $R_1$ is a group according to the formula

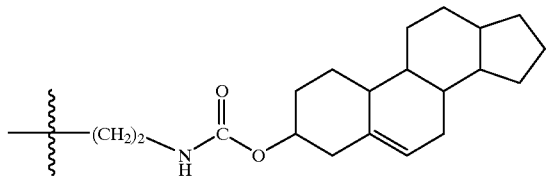

wherein the steroid ring structure can optionally be substituted at one or more steroid ring atoms with one or more substitutents chosen from the group consisting of $C_{1-12}$alkyl, $C_{2-12}$alkenyl, $C_{2-12}$alkynyl, and $C_{3-8}$cycloalkyl and two or more substituents can combine to form additional carbocyclic or heteroalicyclic rings which can be fused or spiro to the steroid ring structure; or $R_1$ is —(CH$_2$)$_2$NHCO$_2$—R, wherein R is a straight chain alkyl group having from about 10 to about 24 carbon atoms.

16. A biodegradable polymeric micelle comprising a biodegradable, amphiphilic polyphosphate having at least one phosphate group in the main chain of the polymer and the polymer having at least one positively charged or positively chargeable group and at least one hydrophobic moiety, wherein the polymer comprises repeat units of the formula:

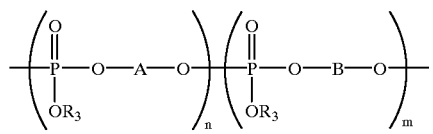

wherein

A and B can be the same or different and are each independently selected from the group consisting of $C_{1-20}$alkylene, $C_{3-20}$cyclic alkylene, $C_{5-20}$arylene, $C_{5-20}$heteroarylene, $C_{3-20}$cyclic heteroalkylene, a hydrophilic divalent linker group, and (CH$_2$CH$_2$O)$_x$CH$_2$CH$_2$—; such that A, B or both A and B comprise a positively charged or positively chargeable functional group in the mainchain and A, B or both A and B can be optionally substituted with one or more neutral or charged hydrophilic groups or hydrophobic groups;

$R_3$ is $C_{1-20}$alkyl, $C_{3-20}$aryl, $C_{3-20}$heteroaryl, $C_{3-8}$heteroalicyclic, $C_{3-8}$cycloalkyl, $C_{7-20}$aralkyl or $C_{3-8}$cycloalkyl $C_{1-20}$alkyl; and each occurrence of $R_3$ can be optionally substituted with one or more neutral or charged groups or one or more hydrophobic moieties;

x is an integer between about 1 and about 100;

m and n are independently selected non-negative integers; and m+n>1.

17. A micelle of claim 16, wherein the positively charged groups are integral to the main chain of the polymer or are present in a phosphate side chain group.

18. A micelle of claim 16, wherein the hydrophobic moieties are groups pendant from the polymer main chain and each hydrophobic group is linked to a phosphate group that is integral to the main chain.

19. A micelle of claim 16, wherein the micelles have a diameter of about 50 nm to about 500 nm.

20. A micelle of claim 16, wherein the micelle can further comprise one or more negatively charged or neutral biologically active substances.

21. A micelle of claim 20, wherein the negatively charged or neutral biologically active substances are selected from the group consisting of DNA, RNA, proteins, and small molecule therapeutics.

22. A micelle of claim 16, wherein the micelle further comprises at least one negatively charged or neutral biologically active substance selected from the group consisting of DNA, RNA, proteins, and small molecule therapeutics.

23. A micelle of claim 22, wherein the micelle further comprises at least one negatively charged or neutral biologically active substance selected from the group consisting of DNA, RNA, proteins, and small molecule therapeutics.

24. A micelle of claim 16, wherein the polymer comprises repeat units according to the formula:

$$\left( \begin{matrix} O \\ \| \\ P-O-R_4-\overset{X^-}{\underset{R_1}{N^+}}-R_5-O \\ | \\ OR_3 \end{matrix} \right)_n \left( \begin{matrix} O \\ \| \\ P-O-A-O \\ | \\ OR_3 \end{matrix} \right)_m$$

wherein $R_4$, $R_5$ and A are each independently chosen from the group consisting of $C_{1-20}$alkylene, $C_{3-20}$cycloalkylene, divalent neutral or charged hydrophilic moieties, $-(CH_2CH_2O)_xCH_2CH_2-$;

x is an integer from 1 to about 100;

$R_1$ is hydrogen, $C_{1-36}$alkyl, $C_{2-36}$alkenyl, $C_{2-36}$alkynyl, $C_{3-20}$cycloalkyl, $C_{3-8}$cycloalkyl$C_{1-36}$alkyl, $C_{7-18}$aralkyl, $C_{3-20}$heteroalicyclic, or $(CH_2)_a-Y-Z$ group;

Y is an $-O-$, $-CO_2-$, $-NHCO_2-$, or $-OCO_2-$ functional group;

Z is $C_{1-36}$alkyl, $C_{2-36}$alkenyl, $C_{2-36}$alkynyl, $C_{3-20}$cycloalkyl, $C_{3-8}$cycloalkyl$C_{1-36}$alkyl, $C_{7-18}$aralkyl, poly(ethylene glycol)-$C_{1-36}$alkyl ether or a steroid derivative;

$R_2$ is absent, hydrogen, $C_{1-36}$alkyl, $C_{3-20}$cycloalkyl, $C_{3-20}$heteroalicyclic, $C_{7-18}$aralkyl, or $C_{3-8}$cycloalkyl $C_{1-36}$alkyl; and $X^-$ is a biocompatible anion.

25. A micelle of claim 16, wherein the polymer comprises repeat units according to the formula:

$$\left( \begin{matrix} O \\ \| \\ P-O-R_4-\overset{X^-}{\underset{R_1}{N^+}}-R_5-O \\ | \\ OR_3 \end{matrix} \right)_n \left( \begin{matrix} O \\ \| \\ P-O-R_8-\overset{X^-}{\underset{R_6}{N^+}}-R_9-O \\ | \\ OR_3 \end{matrix} \right)_m$$

wherein $R_4$, $R_5$, $R_8$ and $R_9$ are independently selected at each occurrence from the group consisting of $C_{1-36}$alkylene, $C_{5-36}$cycloalkylene, and poly(ethyleneglycol) alkyl ether, each occurrence of $R_4$, $R_5$, $R_8$ and $R_9$ can be optionally substituted with a neutral or charged hydrophilic group selected from the group consisting of hydroxyl, hydroxy $C_{1-8}$alkyl, amino $C_{1-8}$alkyl, N—$C_{1-8}$alkyl amino, N,N-di $C_{1-8}$alkyl amino $C_{1-8}$alkyl, amino, N—$C_{1-8}$alkylamino, N,N,di $C_{1-8}$alkylamino, N,N,N-tri $C_{1-8}$alkylamino, amide, carboxylate, sulfate, and phosphate;

$R_2$ and $R_7$ are each independently at each occurrence either absent or are selected from the group consisting of hydrogen, $C_{1-36}$alkyl, $C_{3-20}$cycloalkyl, $C_{3-20}$heteroalicyclic, $C_{7-18}$aralkyl, and $C_{3-8}$cycloalkyl $C_{1-36}$alkyl;

$R_3$ is $C_{1-36}$alkyl, $C_{3-20}$cycloalkyl, $C_{3-20}$heteroalicyclic, $C_{7-18}$aralkyl, or $C_{3-8}$cycloalkyl $C_{1-36}$alkyl;

$R_1$ and $R_6$ are each independently selected groups chosen at each occurrence from the group consisting of hydrogen, $C_{1-36}$alkyl, poly(ethylene glycol) alkyl ether, $(CR_{10}R_{11})_b-Y-Z$;

Y is $-OCO_2-$ or $-_{10}CO_2-$;

Z is alkyl, poly(ethylene glycol) alkyl ether or a steroid derivative;

$R_{10}$ and $R_{11}$ are each independently selected at each occurrence from the group consisting of hydrogen and $C_{1-6}$alkyl;

b is a positive integer;

$m+n \geq 1$; and $n \geq 1$.

26. A micelle of claim 25, wherein the micelle further comprises at least one negatively charged or neutral biologically active substance selected from the group consisting of DNA, RNA, proteins, and small molecule therapeutics.

27. A micelle of claim 16, wherein the polymer comprises repeat units according to the formula:

$$\left( \begin{matrix} O \\ \| \\ P-O-(CH_2)_a-\overset{X^-}{\underset{R_1}{N^+}}-(CH_2)_a-O \\ | \\ OR_3 \end{matrix} \right)_n \left( \begin{matrix} O \\ \| \\ P-O-(CH_2)_a-\overset{X^-}{\underset{R_6}{N^+}}-(CH_2)_a-O \\ | \\ OR_3 \end{matrix} \right)_m$$

wherein $R_2$ and $R_7$ are each independently selected at each occurrence to be absent, hydrogen or $C_{1-20}$alkyl;

$R_1$ and $R_6$ are each independently selected at each occurrence to be hydrogen, $C_{1-36}$alkyl or $(CH_2)_b-N(R_{10})CO_2-Z$.

$R_{10}$ is independently chosen at each occurrence to be hydrogen or $C_{1-6}$alkyl;

Z is independently chosen at each occurrence of Z to be alkyl, $(CH_2CH_2O)_xCH_2CH_3$ or a steroid derivative;

a is an positive integer;

b is a positive integer; and x is an integer from about 1 to about 20.

28. A micelle of claim 27, wherein the micelle further comprises at least one negatively charged or neutral biologically active substance selected from the group consisting of DNA, RNA, proteins, and small molecule therapeutics.

29. A micelle of claim 16, wherein the polymer comprises repeat units according to the formula:

$$\left( \begin{matrix} O \\ \| \\ P-O-R_4-\overset{X^-}{\underset{R_1}{N^+}}-R_5-O \\ | \\ OR_3 \end{matrix} \right)_n$$

wherein $R_1$ is independently selected groups chosen at each occurrence from the group consisting of hydrogen, $C_{1-36}$alkyl, poly(ethylene glycol) alkyl ether, $(CR_{10}R_{11})_b-Y-Z$;

Y is —OCO$_2$— or —NR$_{10}$CO$_2$—;

Z is C$_{1-36}$alkyl, poly(ethylene glycol) alkyl ether or a steroid derivative;

R$_2$ is independently selected at each occurrence to be absent, hydrogen, or a C$_{1-36}$alkyl;

R$_3$ is C$_{1-36}$alkyl;

R$_4$ and R$_5$ are each independently chosen from the group consisting of C$_{1-36}$alkylene, C$_{3-36}$cycloalkylene, divalent neutral or charged hydrophilic moieties, —(CH$_2$CH$_2$O)$_x$CH$_2$CH$_2$;

R$_{10}$ and R$_{11}$ are each independently selected at each occurrence from the group consisting of hydrogen and C$_{1-6}$alkyl;

x is an integer from about 1 to about 100;

X is a biocompatible anion;

b is a positive integer; and n is an integer between about 5 and about 2,000.

30. A micelle of claim 29, wherein the micelle further comprises at least one negatively charged or neutral biologically active substance selected from the group consisting of DNA, RNA, proteins, and small molecule therapeutics.

31. A micelle of claim 29, wherein the polymer comprises repeat units according to the formula:

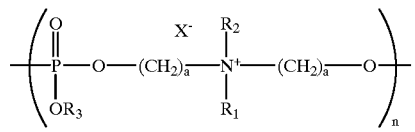

wherein

R$_2$ and R$_3$ are each independently selected C$_{1-6}$alkyl groups;

R$_1$ is independently selected groups chosen at each occurrence from the group consisting of C$_{8-24}$alkyl, poly (ethylene glycol) alkyl ether, (CR$_{10}$R$_{11}$)$_b$—Y—Z;

Y is —OCO$_2$— or —NR$_{10}$CO$_2$—;

Z is alkyl, poly(ethylene glycol) alkyl ether or a steroid derivative;

R$_{10}$ and R$_{11}$ are each independently selected at each occurrence from the group consisting of hydrogen, methyl and ethyl;

X$^-$ is a biocompatible anion;

a is an positive integer;

b is a positive integer; and n is an integer between about 5 and about 2,000.

32. A micelle of claim 31, wherein the micelle further comprises at least one negatively charged or neutral biologically active substance selected from the group consisting of DNA, RNA, proteins, and small molecule therapeutics.

33. A micelle of claim 32, wherein R$_1$ is a group according to the formula

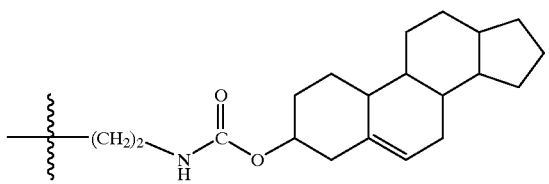

wherein the steroid ring structure can optionally be substituted at one or more steroid ring atoms with one or more substitutents chosen from the group consisting of C$_{1-12}$alkyl, C$_{2-12}$alkenyl, C$_{2-12}$alkynyl, and C$_{3-8}$cycloalkyl and two or more substitutents can combine to form additional carbocyclic or heteroalicyclic rings which can be fused or spiro to the steroid ring structure; or R$_1$ is —(CH$_2$)$_2$NHCO$_2$—R, wherein R is a straight chain alkyl group having from about 10 to about 24 carbon atoms.

34. A micelle of claim 33, wherein the micelle further comprises at least one negatively charged or neutral biologically active substance selected from the group consisting of DNA, RNA, proteins, and small molecule therapeutics.

\* \* \* \* \*